(12) United States Patent
Matsushita et al.

(10) Patent No.: US 10,406,273 B2
(45) Date of Patent: Sep. 10, 2019

(54) BLOOD PURIFICATION APPARATUS

(71) Applicant: Nikkiso Company Limited, Tokyo (JP)

(72) Inventors: Wataru Matsushita, Shizuoka (JP); Kentaro Kogoshi, Shizuoka (JP)

(73) Assignee: Nikkiso Company Limited, Shibuya-ku, Tokyo (JP)

( * ) Notice: Subject to any disclaimer, the term of this patent is extended or adjusted under 35 U.S.C. 154(b) by 121 days.

(21) Appl. No.: 15/451,653

(22) Filed: Mar. 7, 2017

(65) Prior Publication Data

US 2017/0173249 A1 Jun. 22, 2017

Related U.S. Application Data

(63) Continuation of application No. PCT/JP2015/075812, filed on Sep. 11, 2015.

(30) Foreign Application Priority Data

Sep. 12, 2014 (JP) .................................. 2014-186209

(51) Int. Cl.
*A61M 1/14* (2006.01)
*A61M 1/36* (2006.01)
(Continued)

(52) U.S. Cl.
CPC ............ *A61M 1/3638* (2014.02); *A61M 1/14* (2013.01); *A61M 1/1601* (2014.02);
(Continued)

(58) Field of Classification Search
None
See application file for complete search history.

(56) References Cited

U.S. PATENT DOCUMENTS

| 4,331,540 A | 5/1982 | Witsoe |
| 6,044,691 A | 4/2000 | Kenley et al. |

(Continued)

FOREIGN PATENT DOCUMENTS

| EP | 1872813 A1 | 1/2008 |
| JP | S60-153138 A | 10/1985 |

(Continued)

OTHER PUBLICATIONS

Extended European Search Report dated May 30, 2018, Application No. 15839272.0.

(Continued)

*Primary Examiner* — Chester T Barry
(74) *Attorney, Agent, or Firm* — The Dobrusin Law Firm, P.C.; Daniel P. Aleksynas

(57) ABSTRACT

A blood purification apparatus that is capable of performing a liquid spill prevention operation and uniformizing the amount of air introduced through an opened portion. The blood purification apparatus includes a dialysate introduction line that allows dialysate to be introduced into a dialyzer; a dialysate discharge line that allows the dialysate to be discharged from the dialyzer; coupling tools that allow free switching between a connected state which causes a closed circuit, and an opened state which causes the closed circuit to be opened to form an opened portion; and a control means that performs a liquid spill prevention operation in which external air is introduced through the opened portion. An air detection means, by which air introduced through the opened portion is detectable, is provided in the vicinity of the coupling tools, and the control means stops the liquid spill prevention operation when air is detected by the air detection means.

17 Claims, 22 Drawing Sheets

(51) Int. Cl.
*A61M 1/16* (2006.01)
*A61M 1/26* (2006.01)

(52) U.S. Cl.
CPC ............ *A61M 1/168* (2013.01); *A61M 1/169* (2013.01); *A61M 1/267* (2014.02); *A61M 1/3659* (2014.02); *A61M 2205/3306* (2013.01); *A61M 2205/3375* (2013.01)

(56) References Cited

U.S. PATENT DOCUMENTS

| | | |
|---|---|---|
| 2006/0079826 A1 | 4/2006 | Beden et al. |
| 2009/0024070 A1 | 1/2009 | Gelfand et al. |
| 2009/0043240 A1 | 2/2009 | Robinson et al. |
| 2010/0168640 A1 | 7/2010 | Kopperschmidt et al. |
| 2010/0274172 A1 | 10/2010 | Guenther et al. |
| 2011/0139690 A1 | 6/2011 | Akita et al. |
| 2012/0000547 A1 | 1/2012 | Gronau et al. |
| 2013/0035626 A1 | 2/2013 | Suzuki |
| 2015/0021244 A1 | 1/2015 | Furuhashi et al. |
| 2015/0151036 A1 | 6/2015 | Furuhashi et al. |
| 2016/0250405 A1 | 5/2016 | Kogoshi et al. |

FOREIGN PATENT DOCUMENTS

| | | |
|---|---|---|
| JP | 2004-016619 A | 1/2004 |
| JP | 2005-253555 A | 4/2006 |
| JP | 2006-280775 A | 10/2006 |
| JP | 2007-007435 A | 1/2007 |
| JP | 2007-167108 A | 7/2007 |
| JP | 2007-282737 A | 6/2008 |
| JP | 2009-112651 A | 5/2009 |
| JP | 2009-131412 A | 6/2009 |
| JP | 2010-000161 A | 1/2010 |
| JP | 2010-269050 A | 12/2010 |
| JP | 2010-273693 A | 12/2010 |
| JP | 2010-273784 A | 12/2010 |
| JP | 2011-161059 A | 8/2011 |
| JP | 2012-192099 A | 10/2012 |
| JP | 2013-056079 A | 3/2013 |
| JP | 2014-097197 A | 5/2014 |
| JP | 2014097197 A | 5/2014 |
| WO | 2011/099521 A1 | 5/2011 |
| WO | 2013/031965 A1 | 3/2013 |
| WO | 2015/068833 A1 | 5/2015 |

OTHER PUBLICATIONS

Potentially related U.S. Appl. No. 14/497,369, filed Sep. 26, 2014, published as US2015/0021244 on Jan. 22, 2015.
Potentially related U.S. Appl. No. 14/615,839, filed Feb. 6, 2015, published as US2015/0151036 on Jun. 4, 2015.
Potentially related U.S. Appl. No. 15/149,247, filed May 9, 2016, published as US2016/0250405 on Sep. 1, 2016.

[Fig 1]
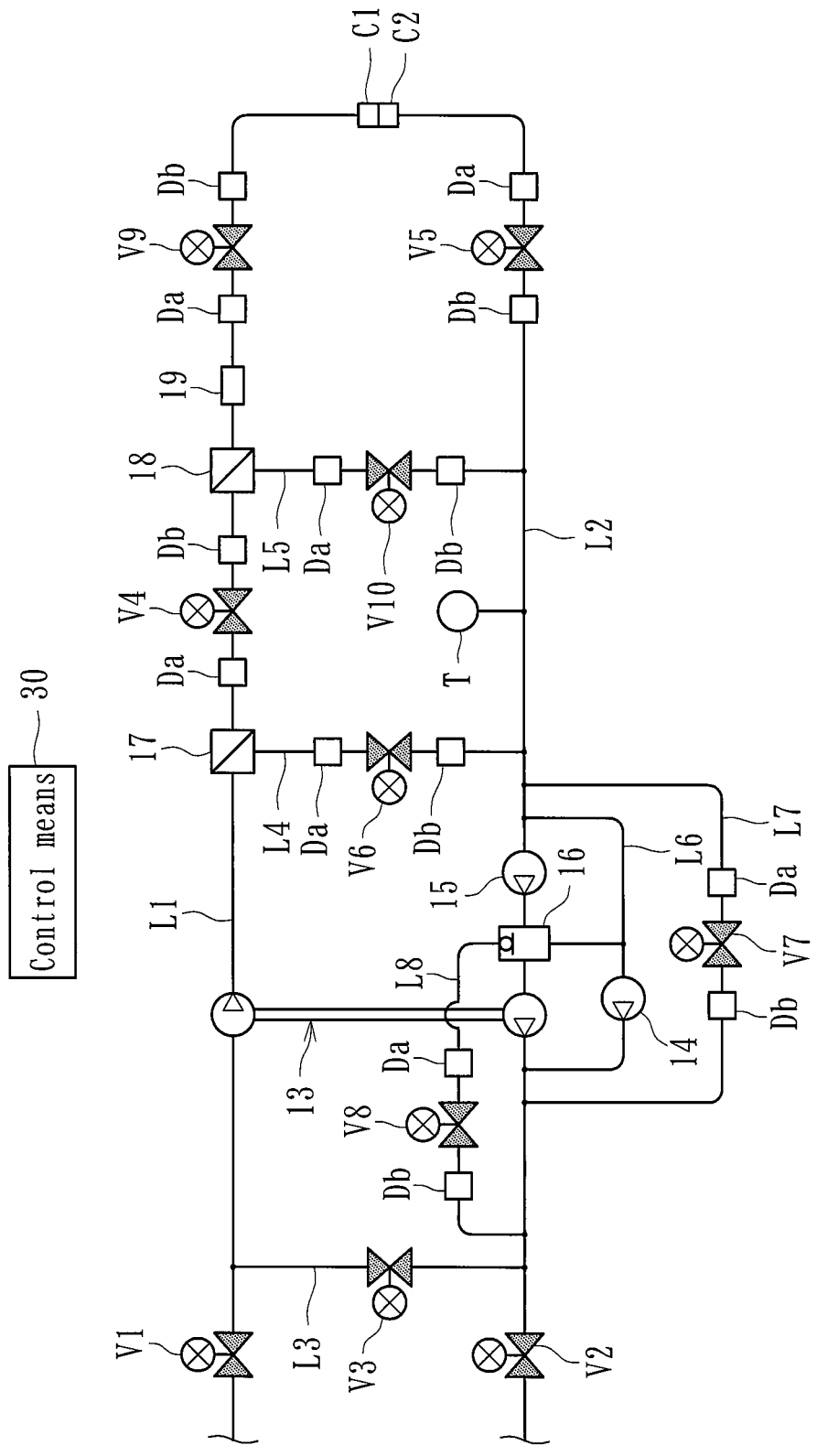

[Fig 2]
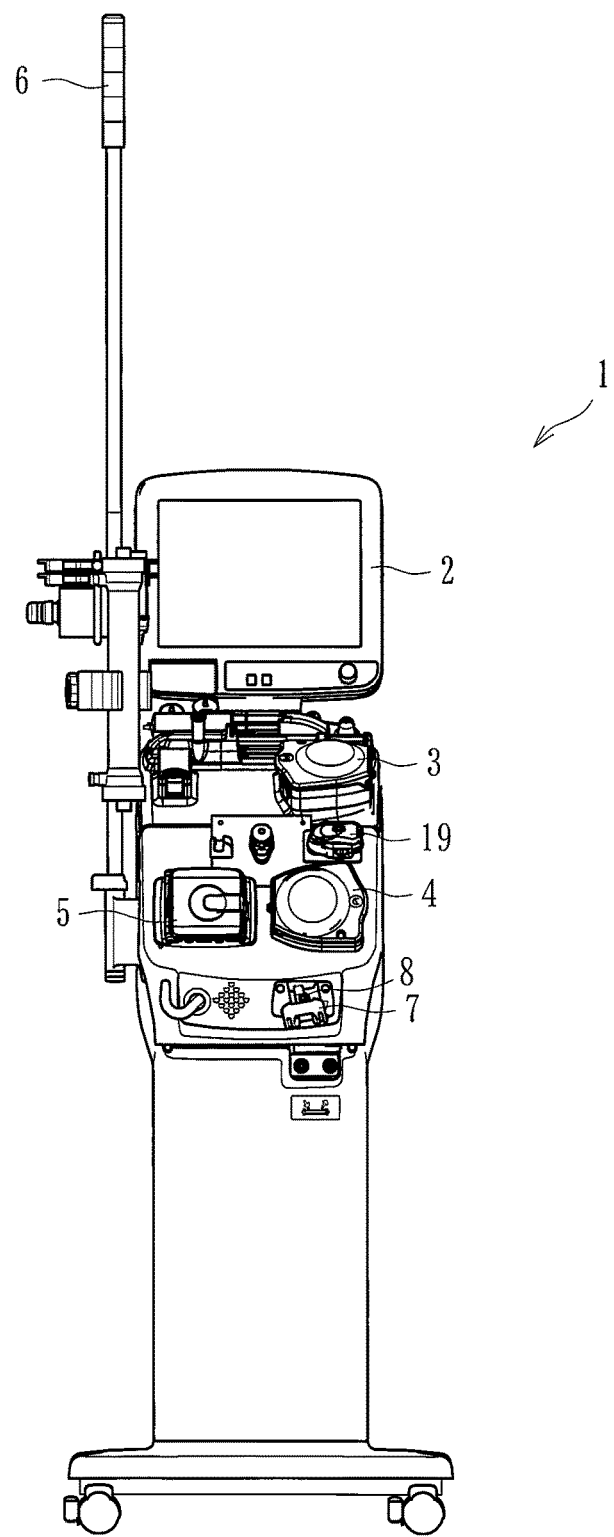

[Fig 3]
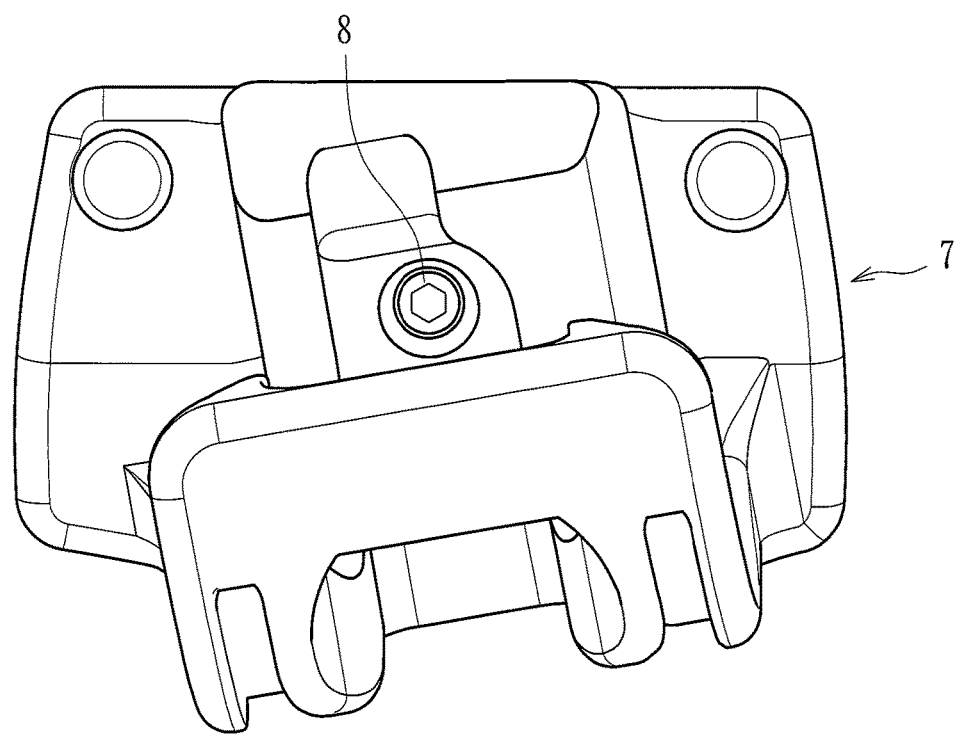

[Fig 4]
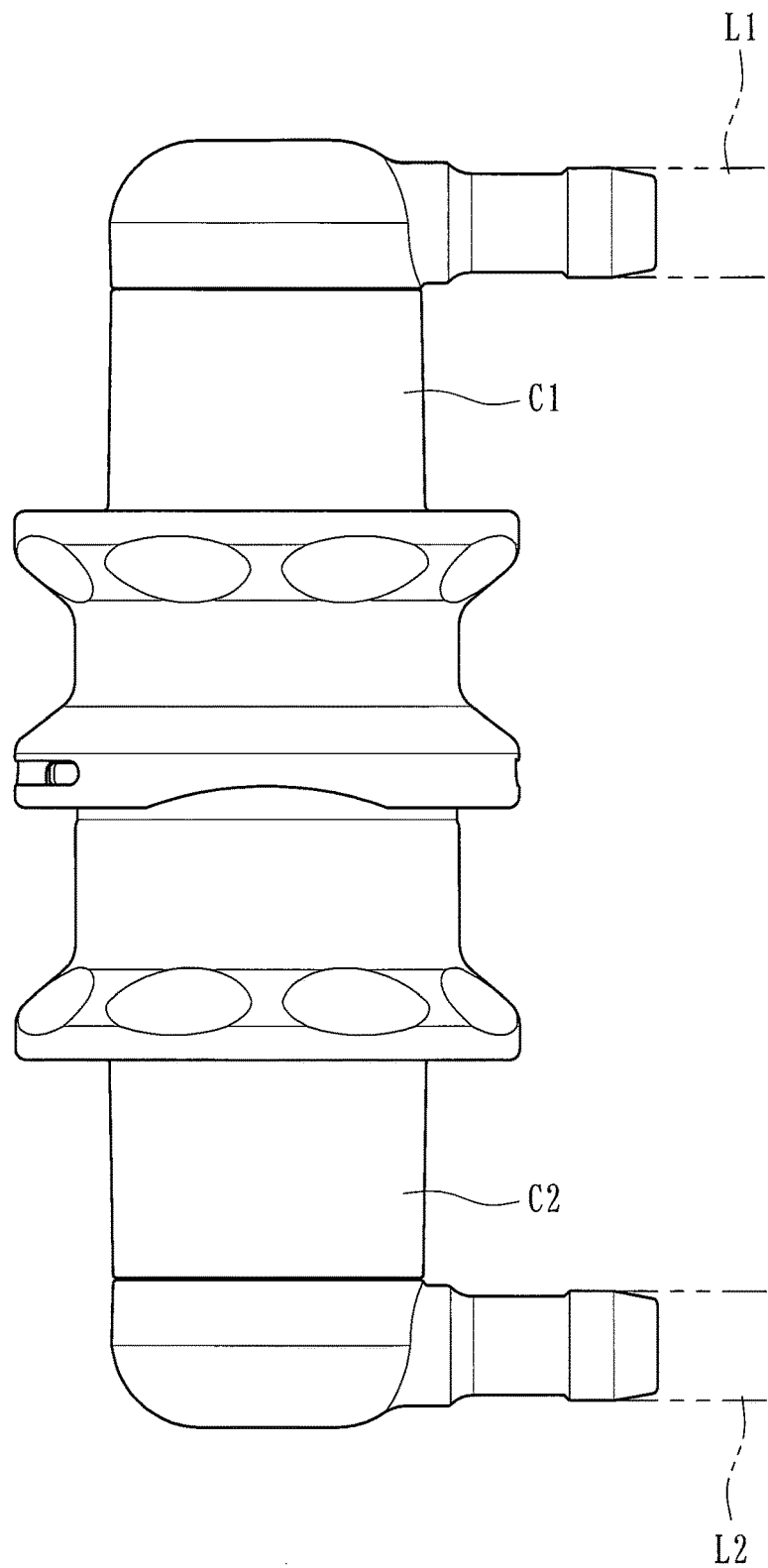

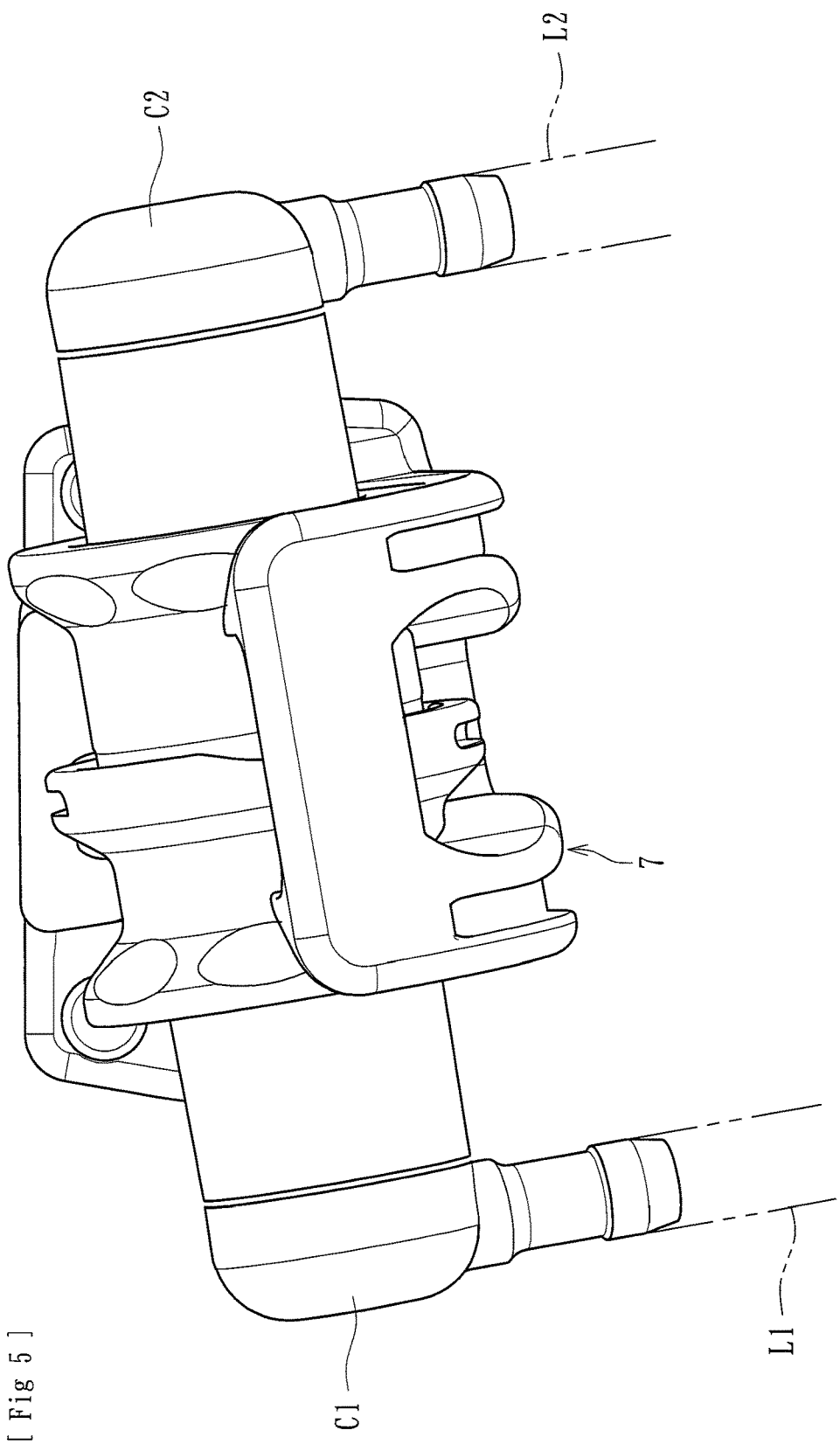
[Fig 5]

[Fig 6]
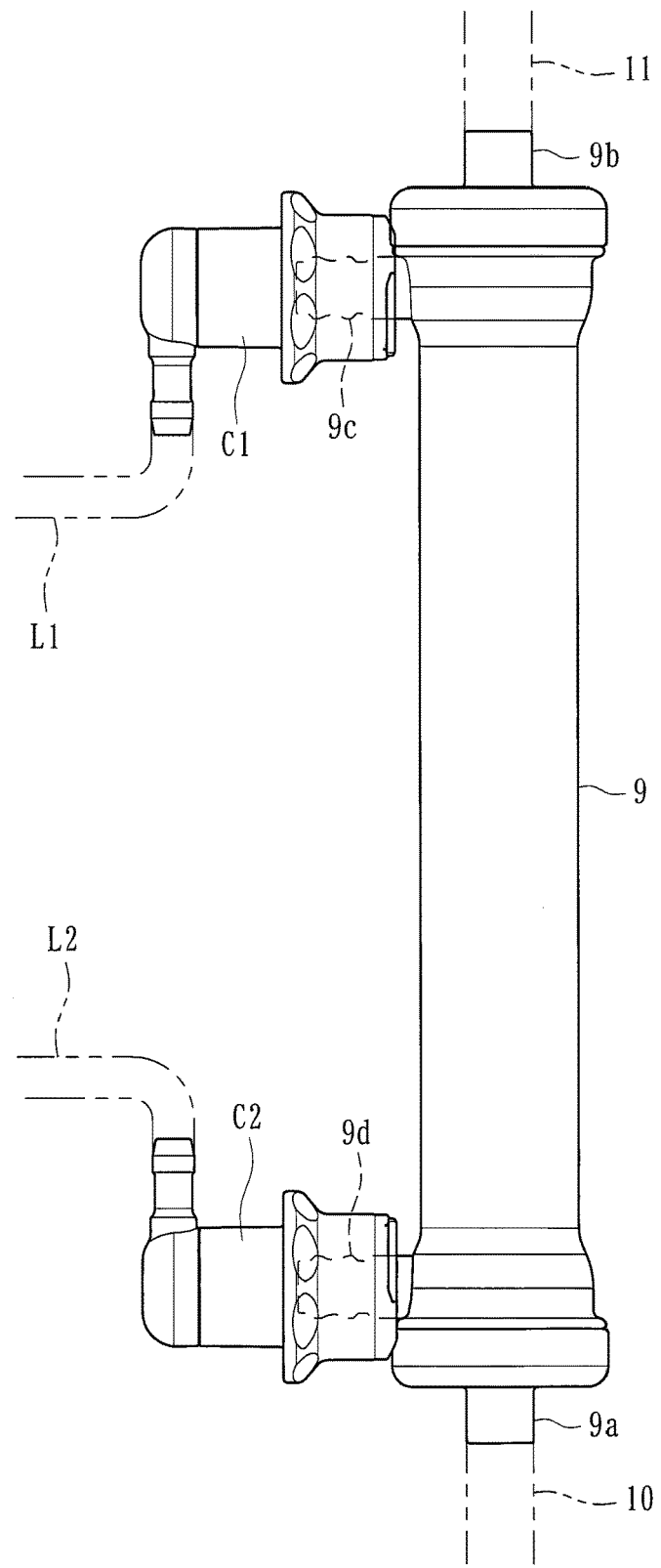

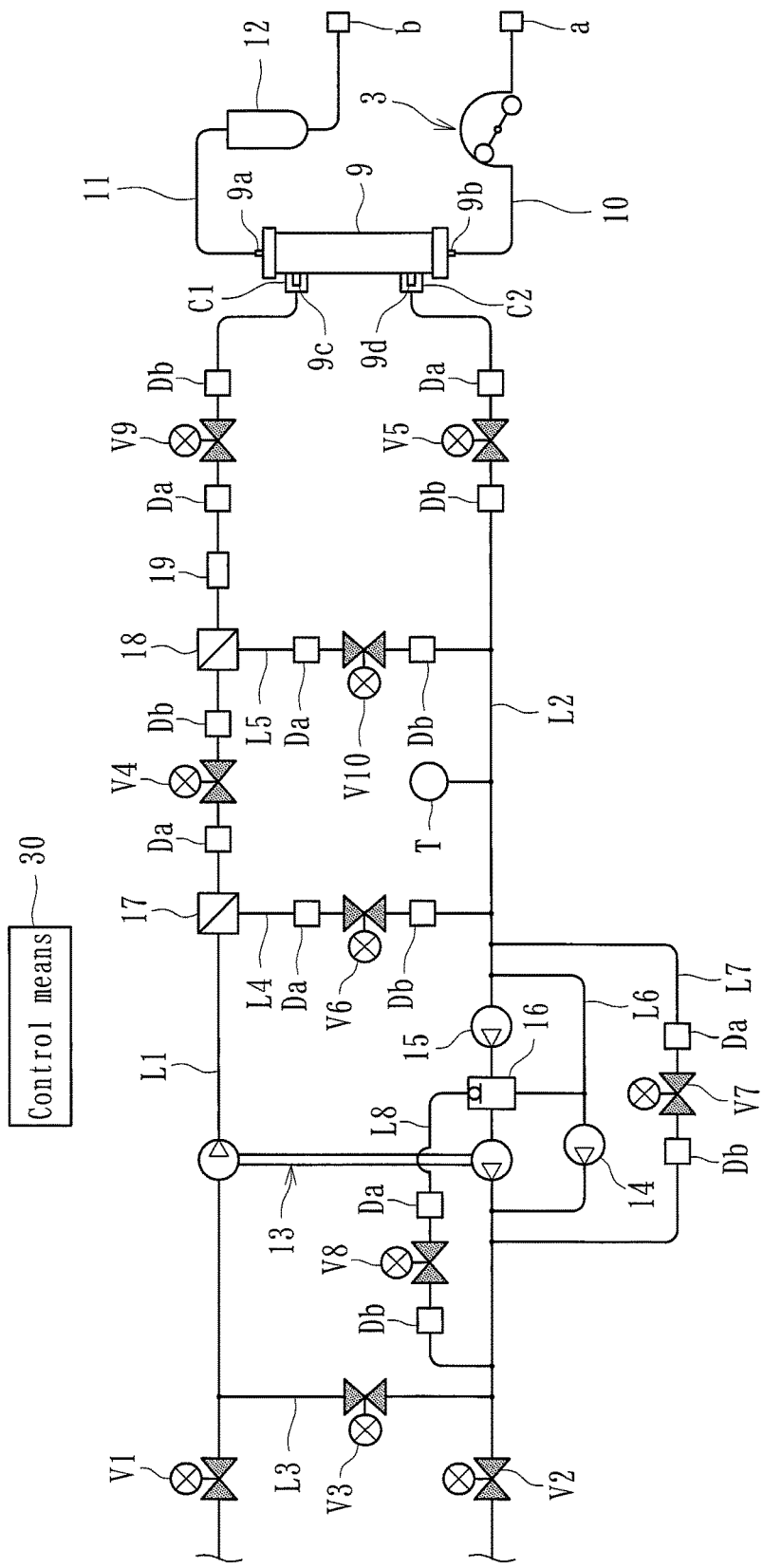
[Fig 7]

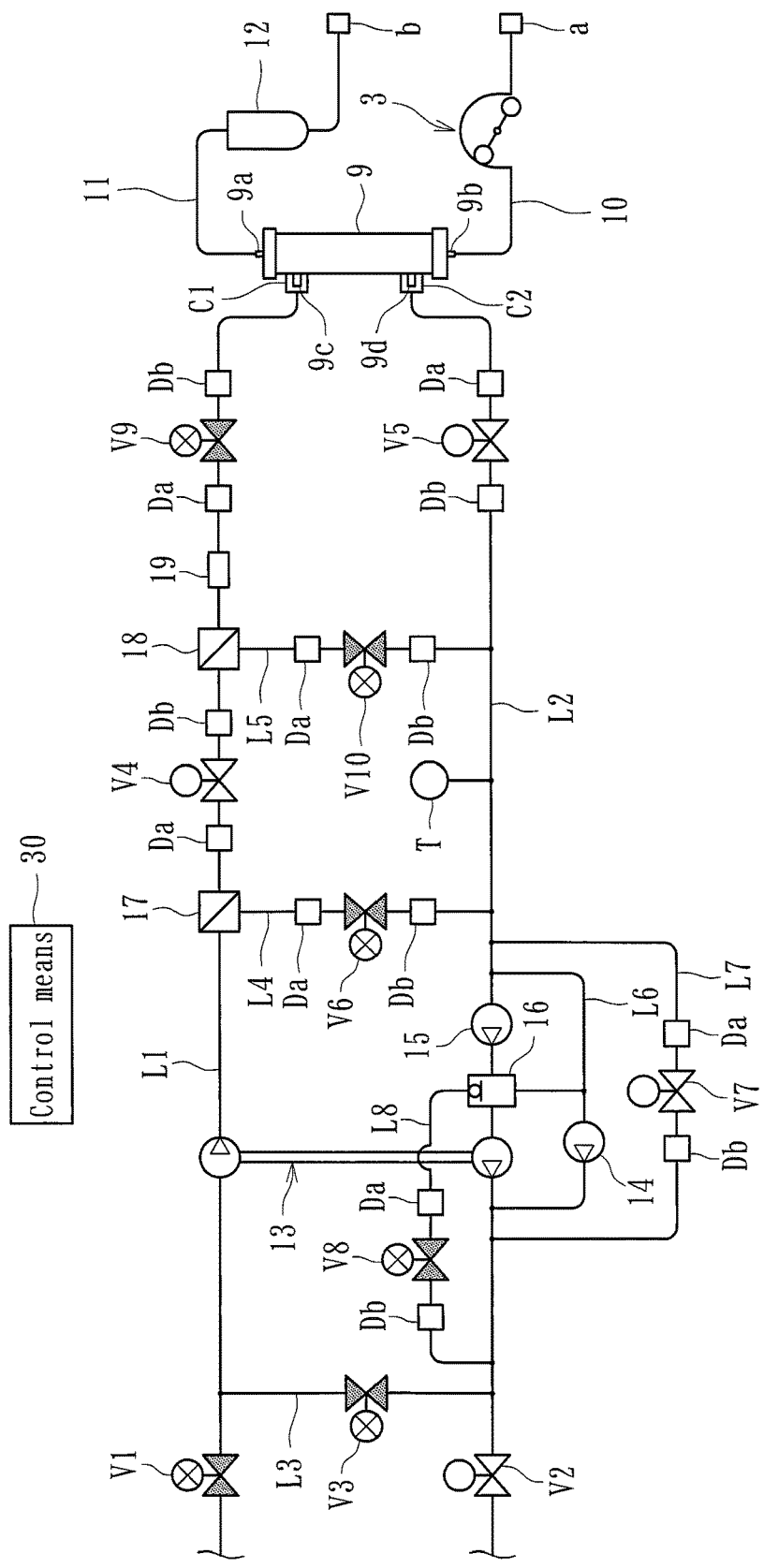
[Fig 8]

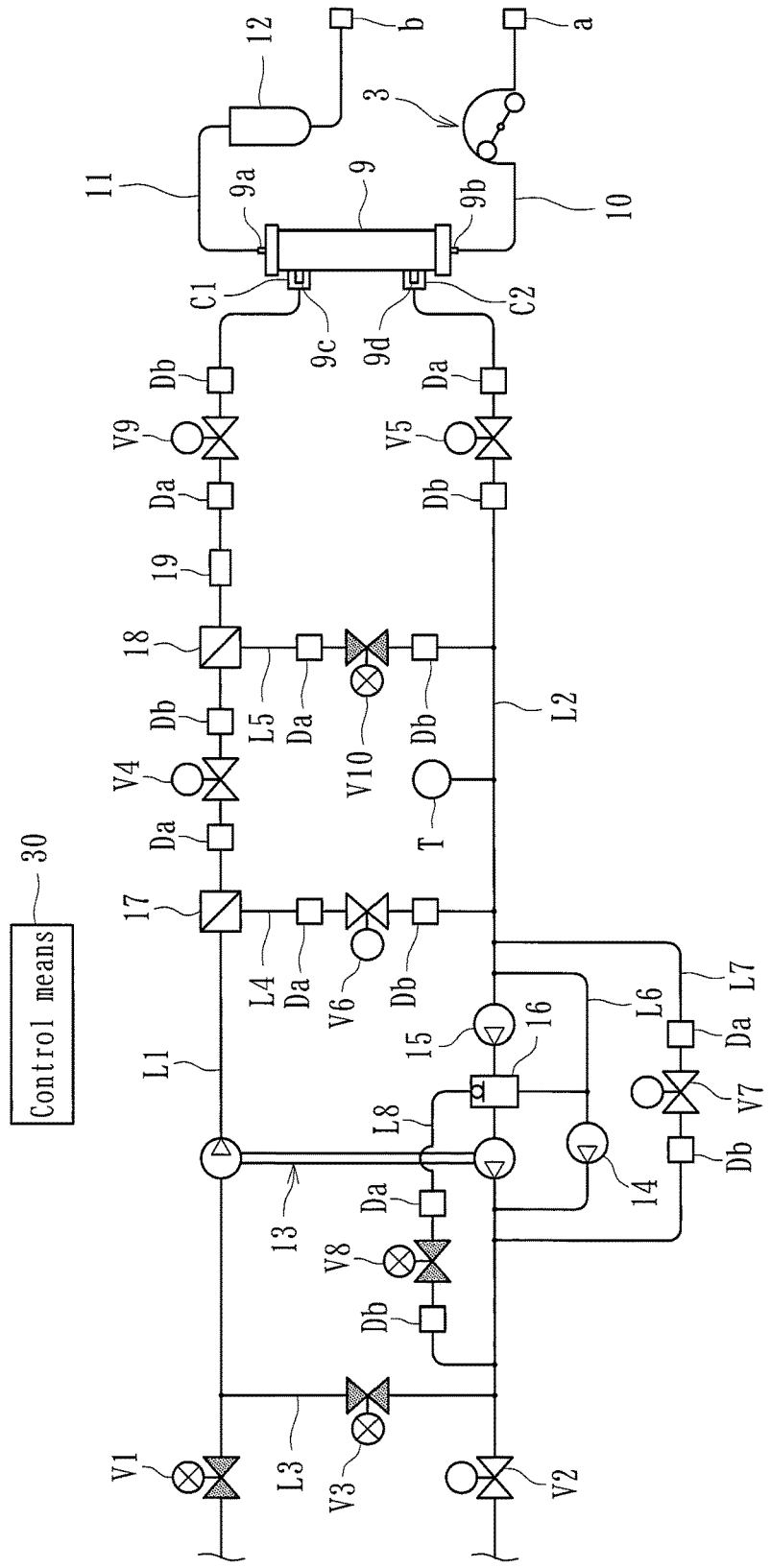
[Fig 9]

[Fig 10]
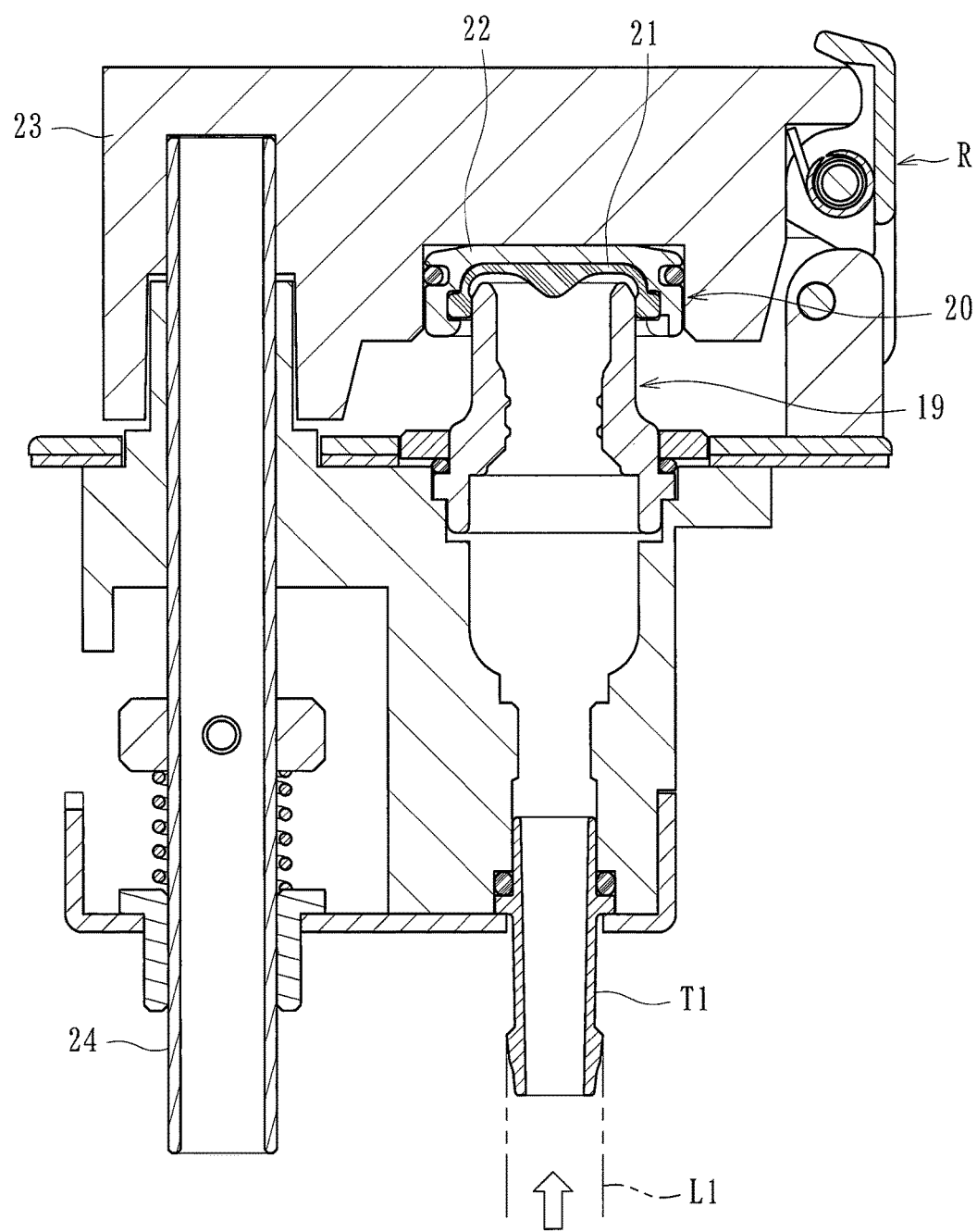

[Fig 11]
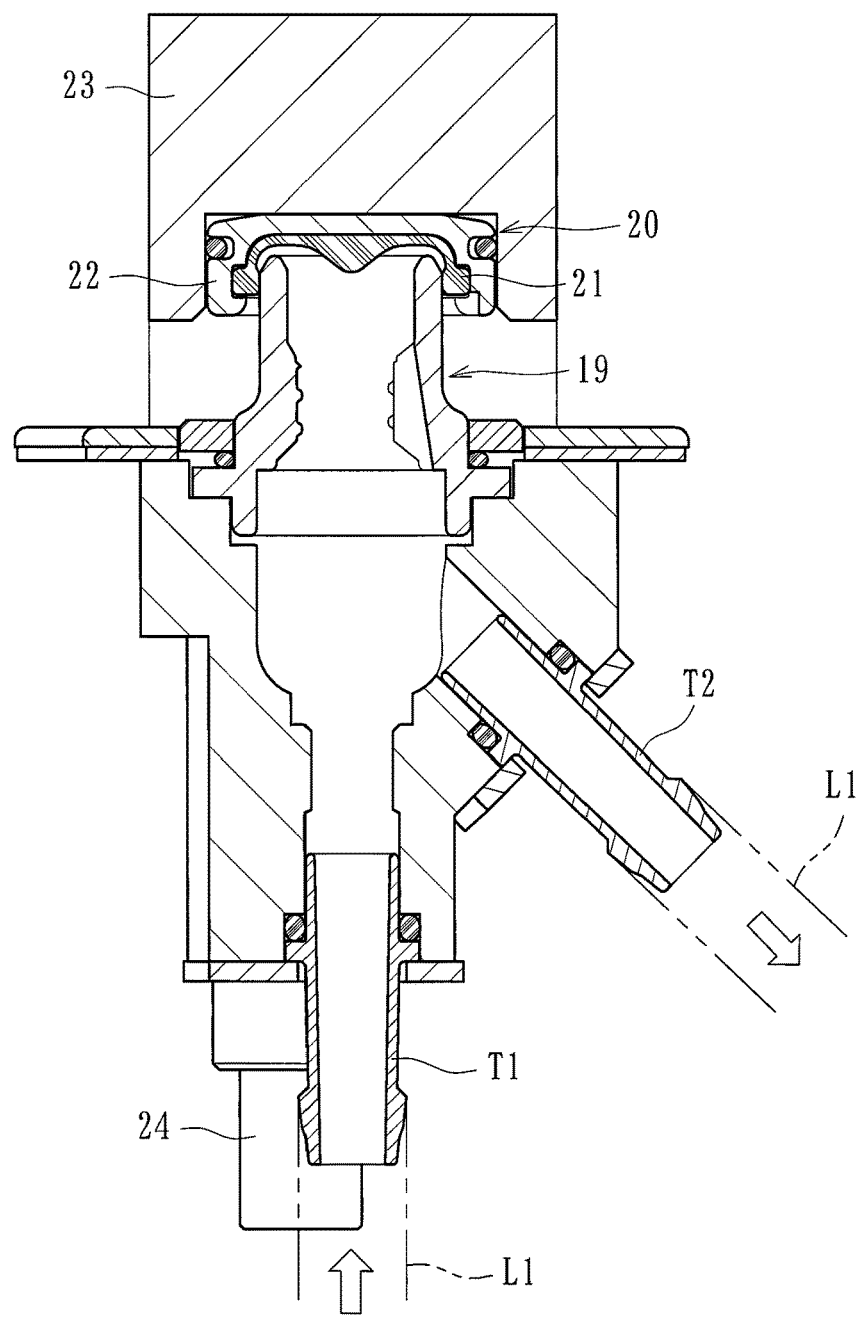

[Fig 12]
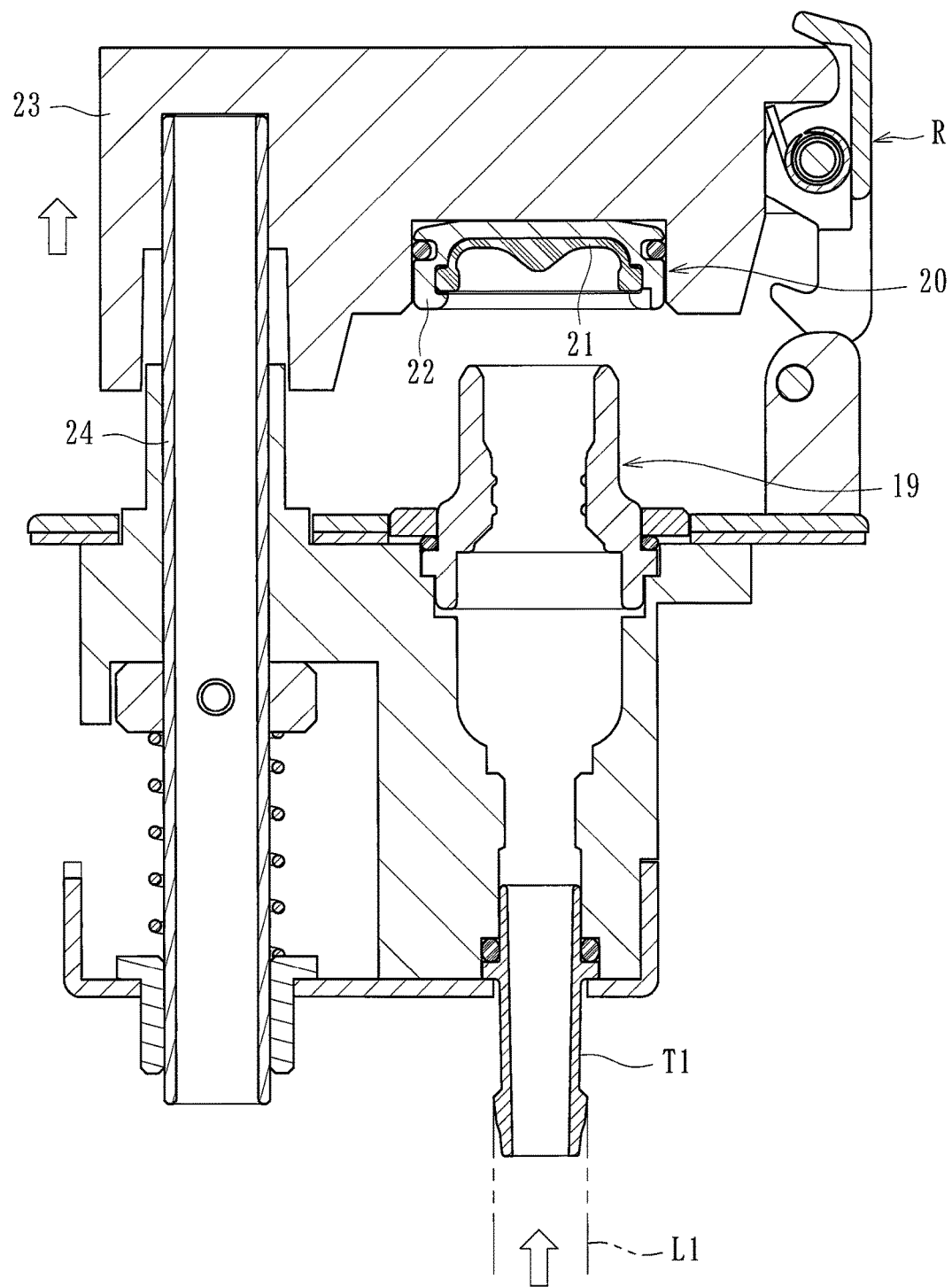

[Fig 13]
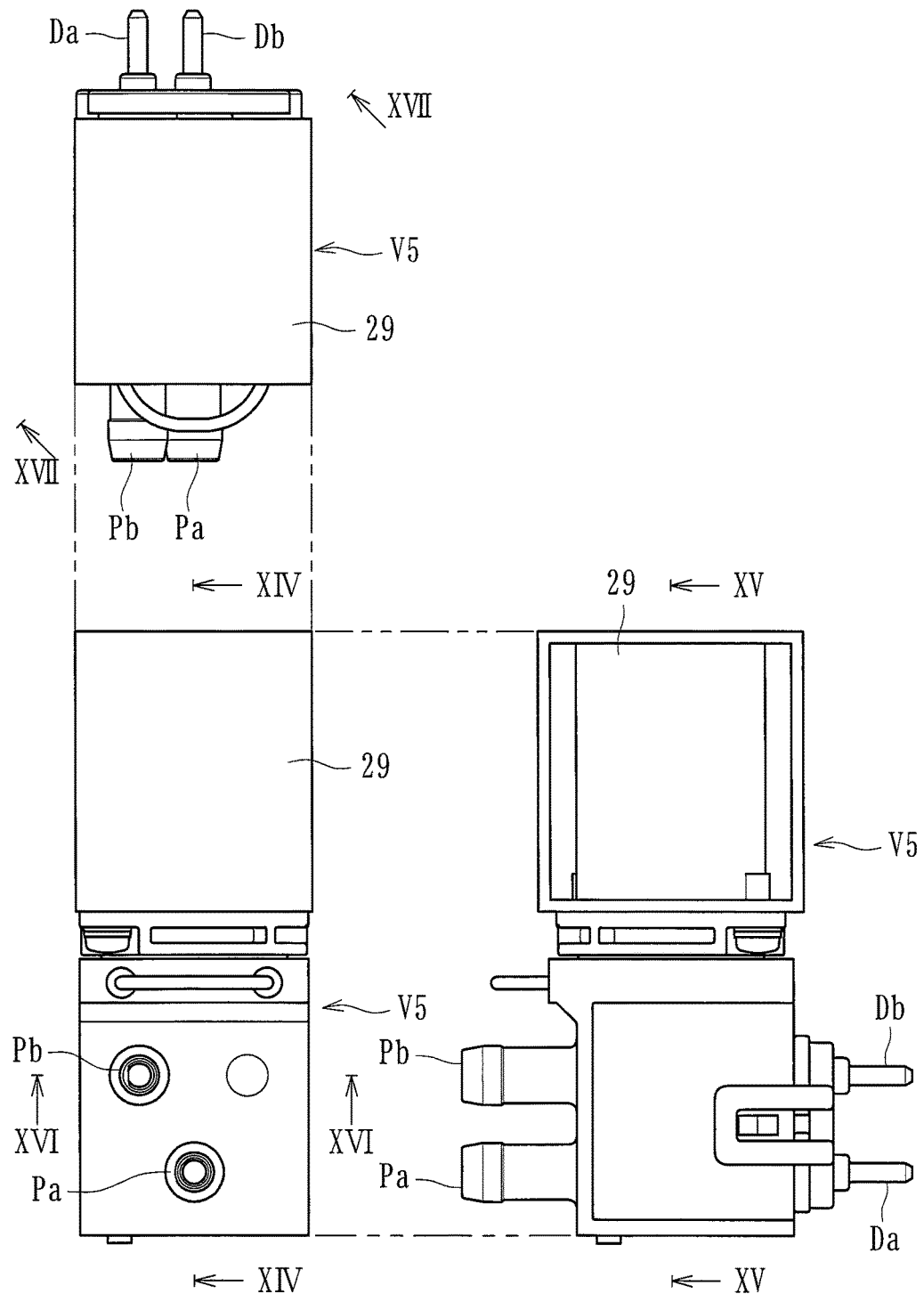

[Fig 14]
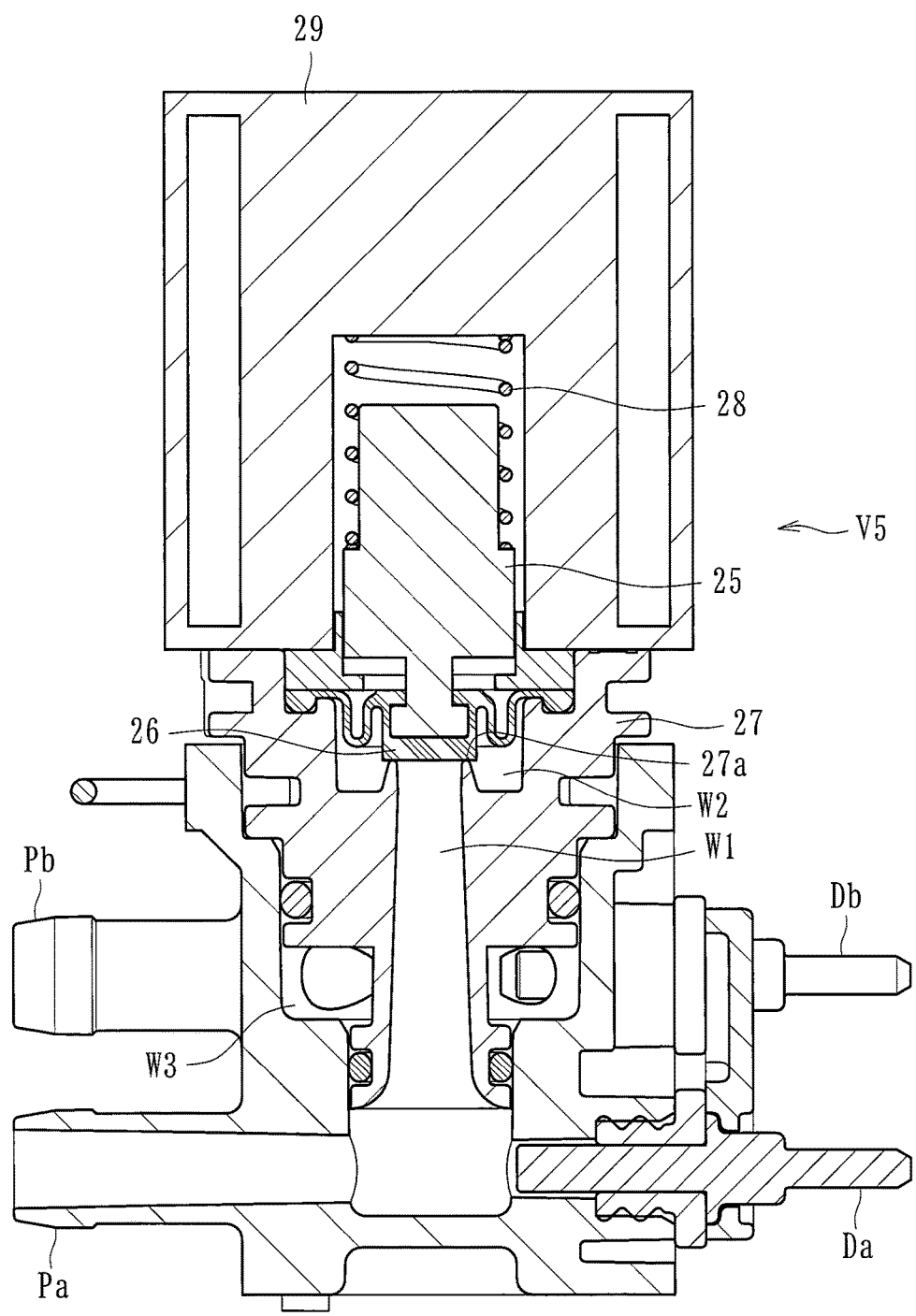

[Fig 15]
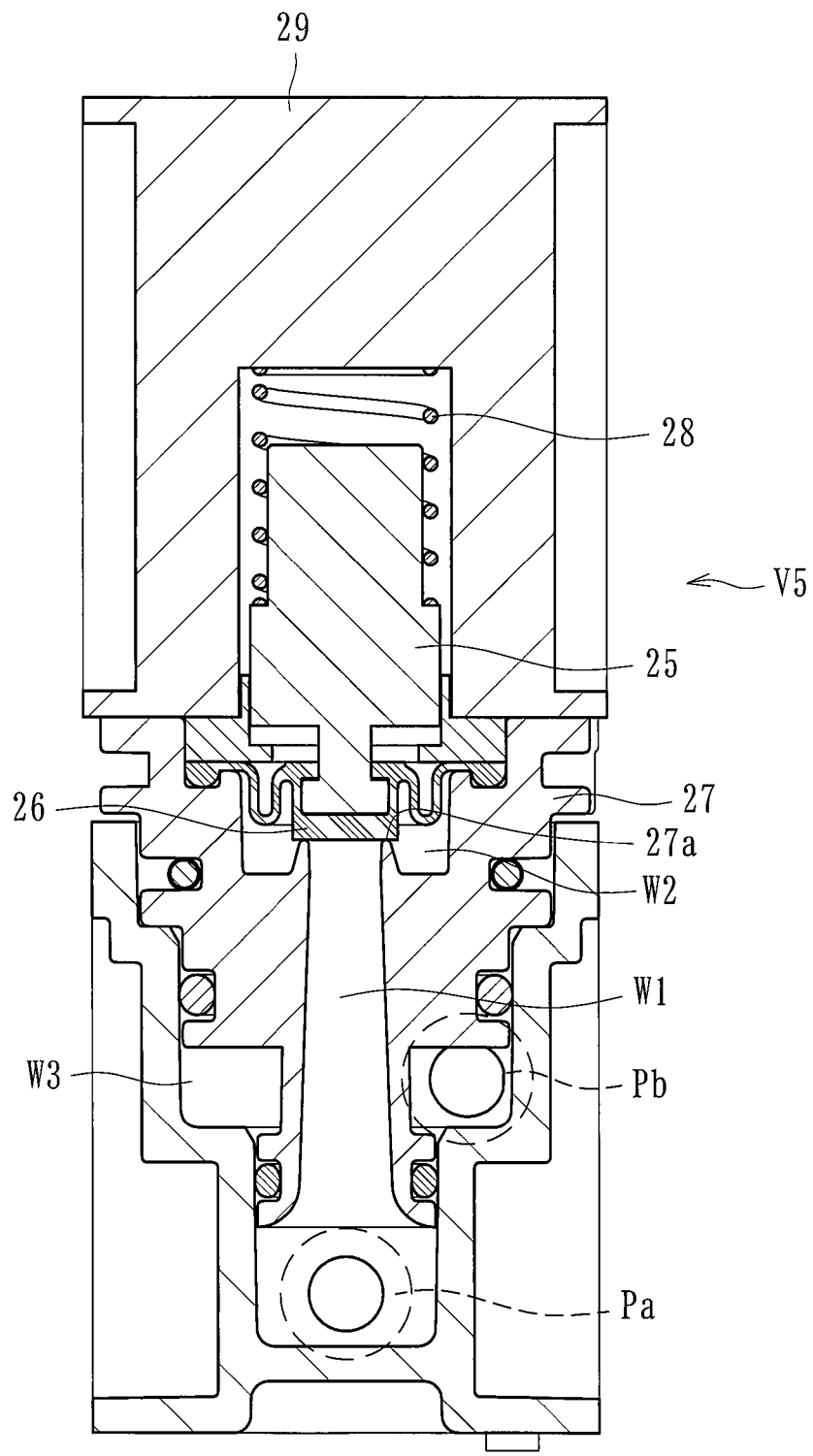

[Fig 16]
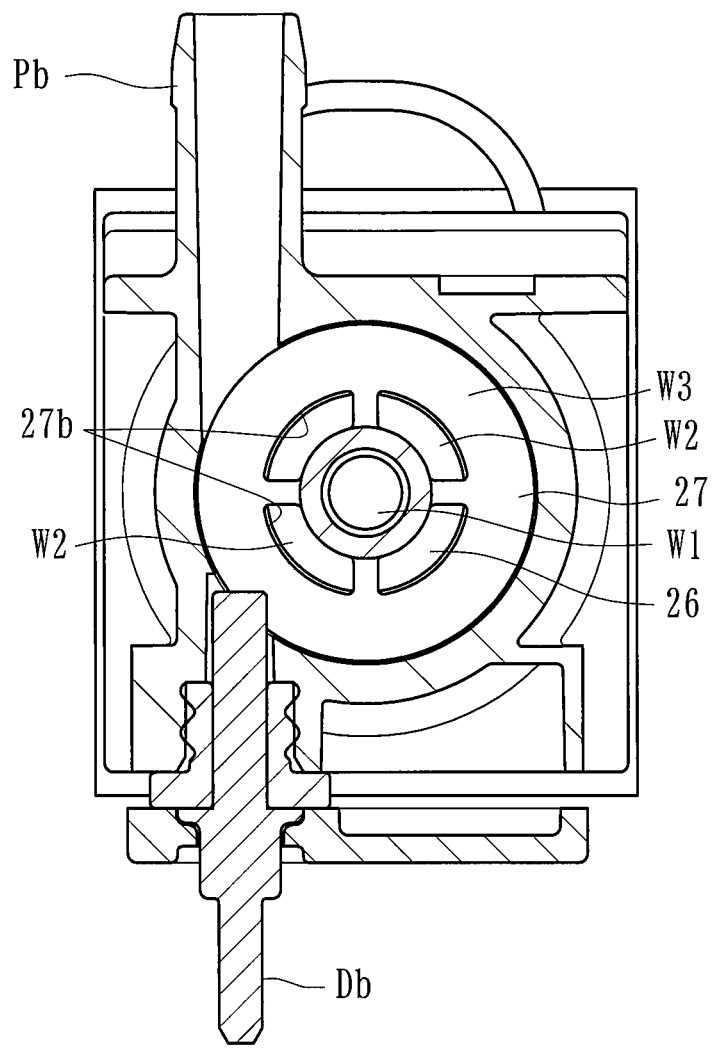

[Fig 17]
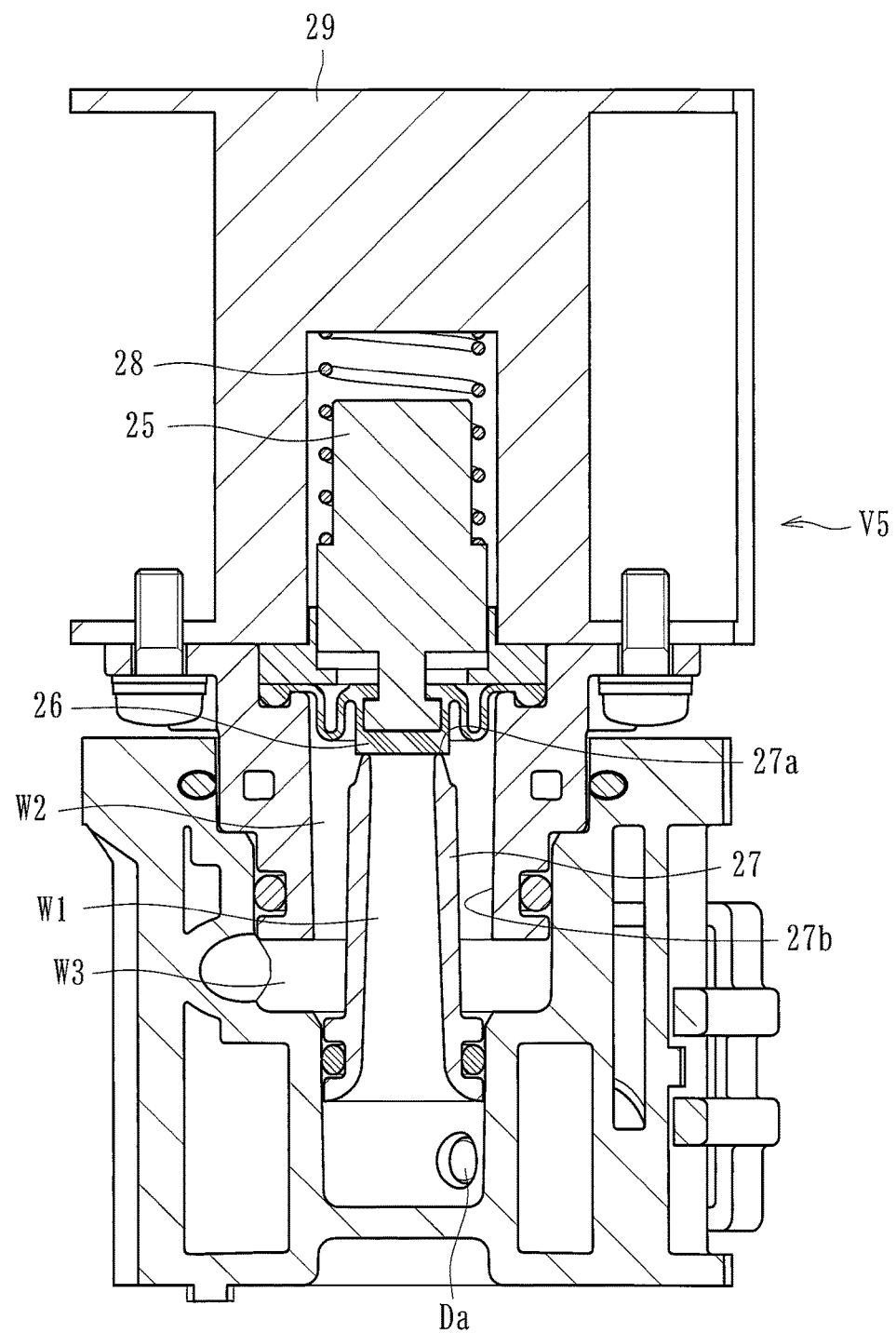

[ Fig 18 ]
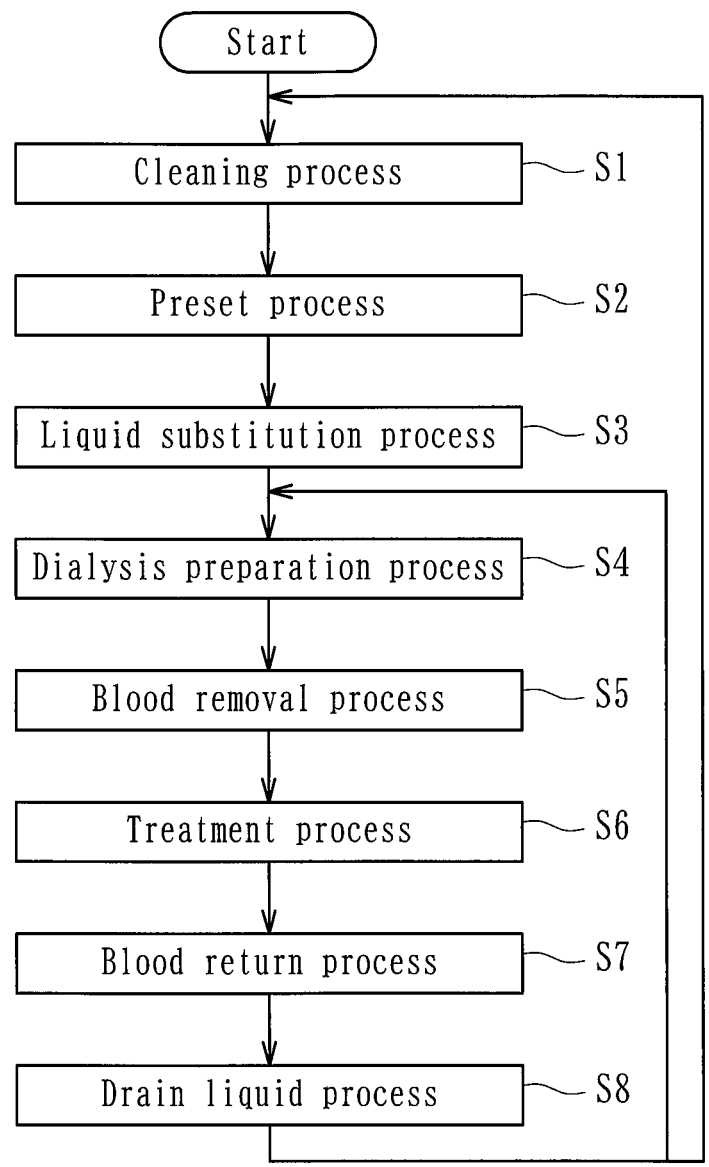

[ Fig 19 ]
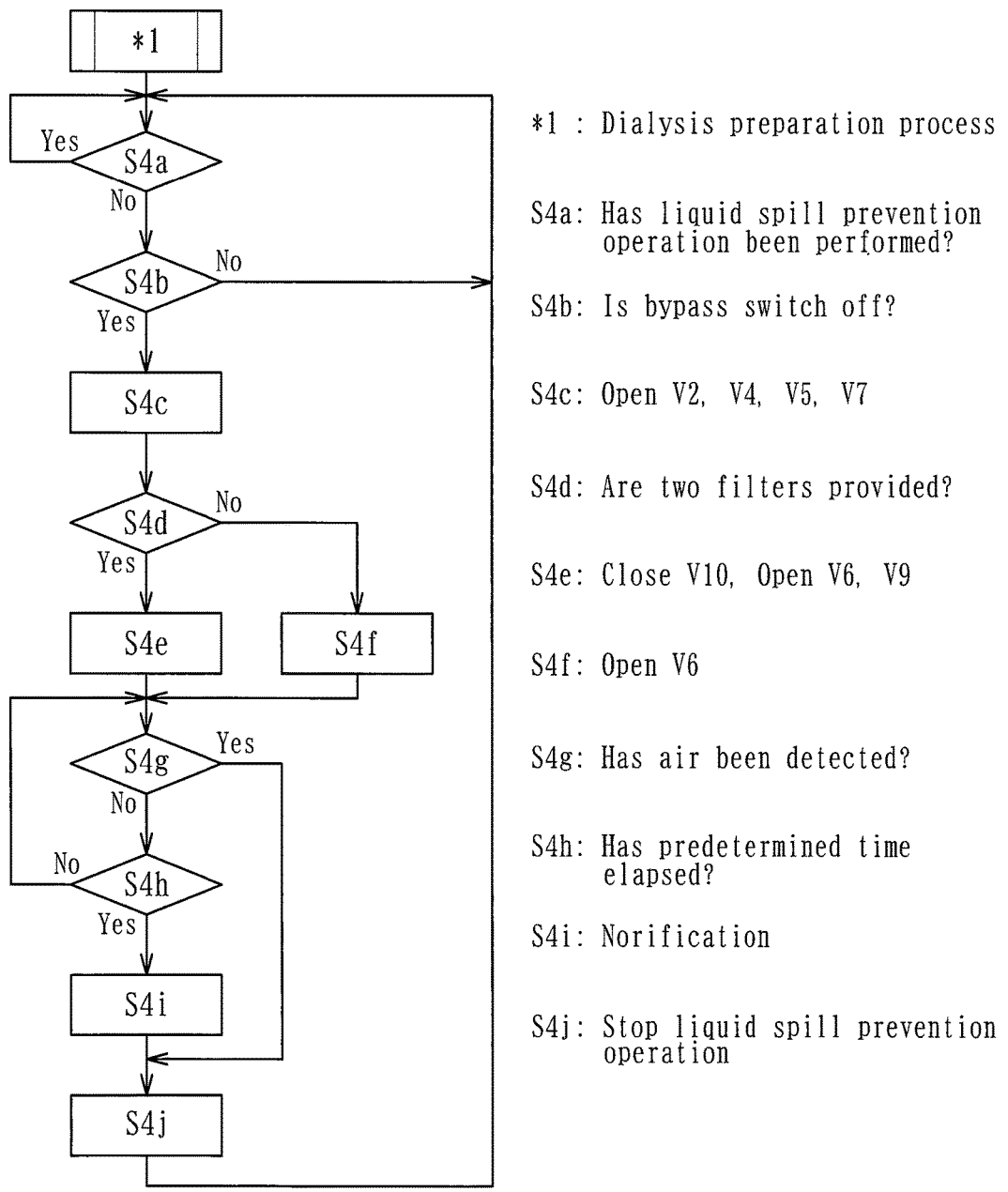
*1 : Dialysis preparation process
S4a: Has liquid spill prevention operation been performed?
S4b: Is bypass switch off?
S4c: Open V2, V4, V5, V7
S4d: Are two filters provided?
S4e: Close V10, Open V6, V9
S4f: Open V6
S4g: Has air been detected?
S4h: Has predetermined time elapsed?
S4i: Norification
S4j: Stop liquid spill prevention operation

[Fig 20]
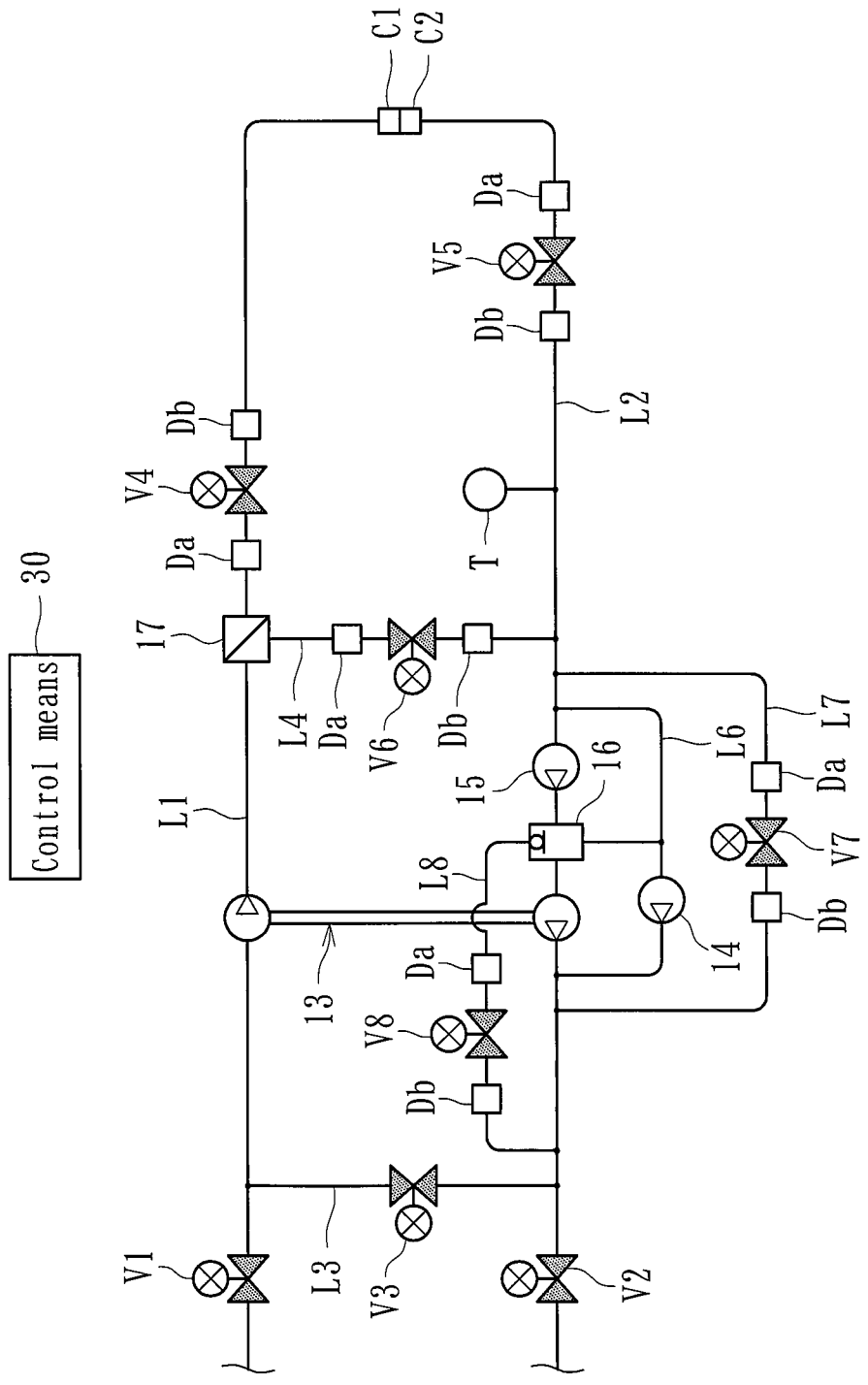

[Fig 21]
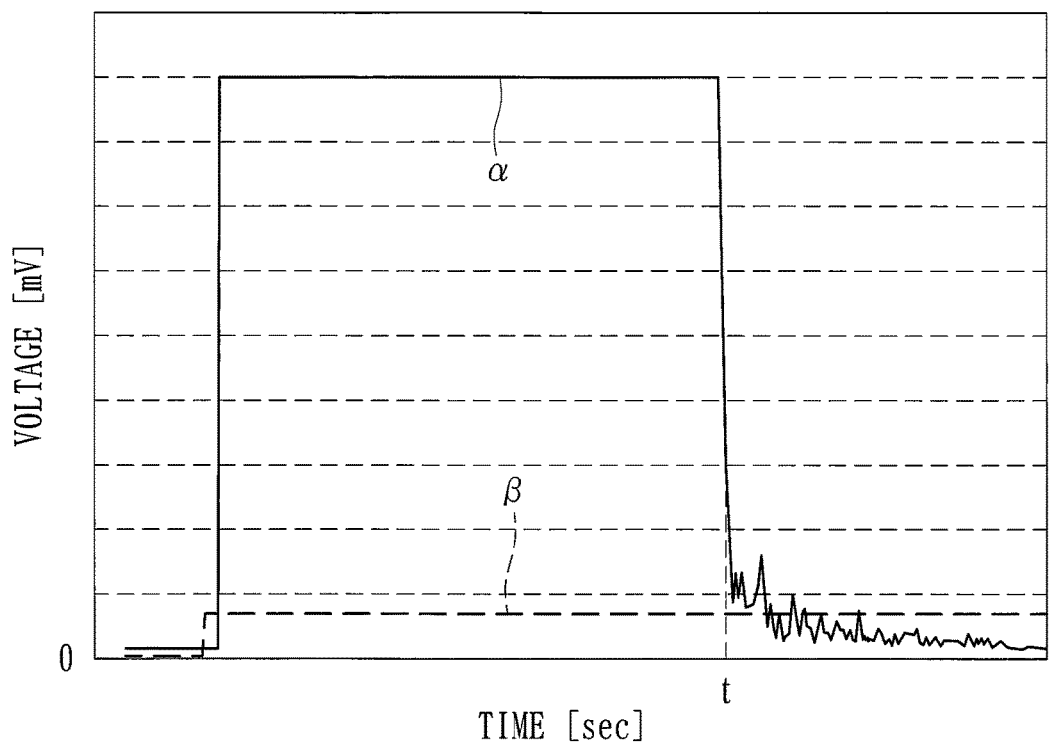

[ Fig 22 ]
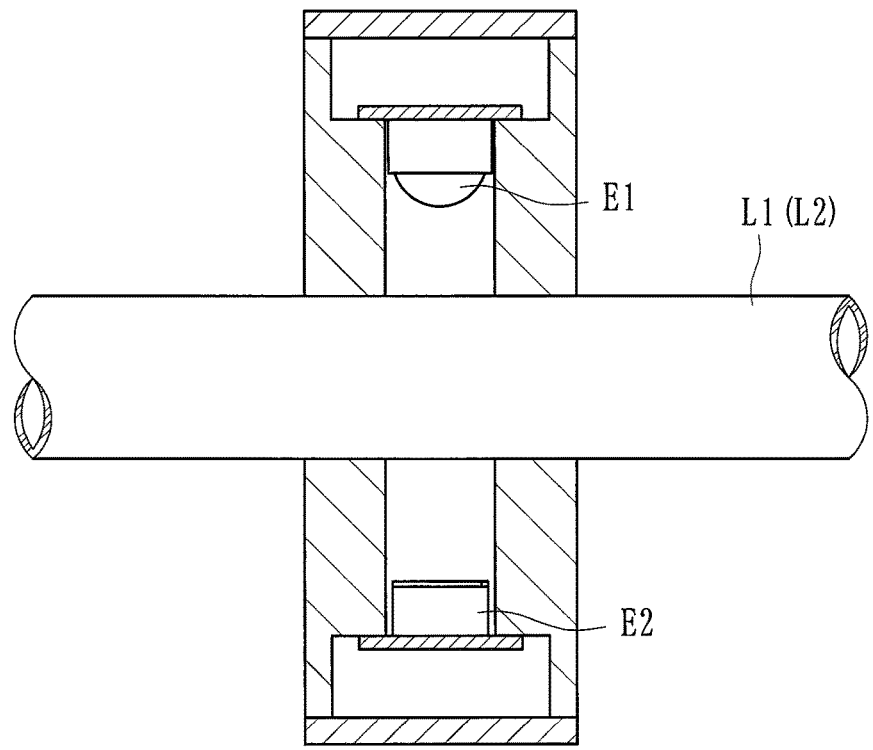
[ Fig 23 ]
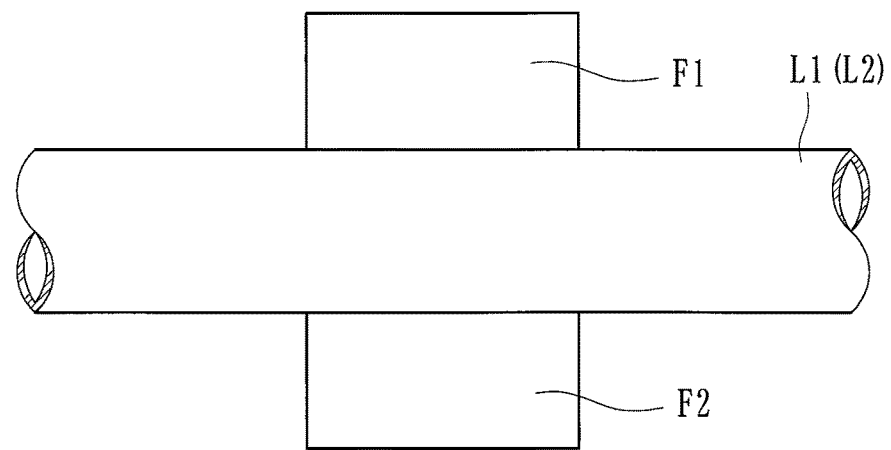

BLOOD PURIFICATION APPARATUS

FIELD

The present invention relates to a blood purification apparatus that includes a coupling means that allows free switching between a connected state which causes a dialysate introduction line and a dialysate discharge line to form a closed circuit, and an opened state which causes the closed circuit to be opened to form an opened portion, and when the connected state is switched to the opened state by the coupling means, a liquid spill prevention operation is performed, in which external air is introduced through the opened portion.

BACKGROUND

A hemodialysis treatment is a treatment in which the blood of a patient is extracorporeally circulated to purify the blood. In such hemodialysis treatment, a dialysis device and a dialyzer as a blood purifier that allows dialysate to flow are used, and a blood circuit, which causes the blood of a patient to be extracorporeally circulated, is connected to the dialyzer, the blood and dialysate are brought into contact with each other via a semipermeable membrane of the dialyzer, and the waste and excess water in the blood can be removed (removal of excess water is referred to as "ultrafiltration"). A configuration is adopted in which the blood purified by the dialyzer is returned to the body of the patient via a puncture needle, whereas the waste and excess water are discharged to the outside along with the dialysate.

The dialysis device has a dialysate introduction line through which dialysate is introduced into the dialyzer, and a dialysate discharge line through which the dialysate introduced into the dialyzer is discharged along with the waste and excess water, and coupling tools (coupling) which can be coupled to the dialyzer are respectively attached to the leading end of the dialysate introduction line and the leading end of the dialysate discharge line. These coupling tools are configured to form a closed circuit with the dialysate introduction line and the dialysate discharge line by connecting to each other when treatment is not made, and when treatment is started (or when preparation for dialysis is made), the connection is released, and thus the coupling tools each can be coupled to the dialyzer (for instance, see PTL 1).

PATENT LITERATURE

PTL 1: Japanese Unexamined Patent Application Publication No. 2014-97197

SUMMARY

In the above-described conventional technique, when connection between the coupling tools is released at the start of treatment, dialysate may overflow to the outside from the leading end of the dialysate introduction line or the leading end of the dialysate discharge line. Specifically, in a state in which the coupling tools are connected to each other, the dialysate introduction line and the dialysate discharge line form a closed circuit, thus when the connection between the coupling tools is released, the closed circuit is opened and the dialysate overflows to the outside through an opened portion, that is the leading end of the dialysate introduction line or the leading end of the dialysate discharge line.

In order to avoid such a problem, a liquid spill prevention operation may be performed in which when the connection between the coupling tools is released to open the closed circuit, the base end side of the dialysate introduction line or the dialysate discharge line is opened, and the difference of height (head difference) between the coupling tools and the dialysate introduction line or the dialysate discharge line causes the dialysate to be discharged to the outside, and thus air is introduced through the leading end of the dialysate introduction line or the leading end of the dialysate discharge line, which is an opened portion. When the connection between the coupling tools is released, the dialysate can be prevented from spilling to the outside by performing the liquid spill prevention operation for a certain time.

However, when the liquid spill prevention operation is performed as describe above, since the difference of height between the coupling tools and the dialysate introduction line or the dialysate discharge line causes the dialysate to be discharged to the outside, and air in the amount of the discharged dialysate is introduced through the opened portion, the amount of the air introduced is not uniformized and it is difficult to introduce a desired amount of air. Thus, when the amount of introduced air is too small, a liquid spill prevention effect is insufficient, whereas when the amount of introduced air is too large, for instance, air may reach the vicinity of a liquid pressure sensor which measures a liquid pressure within the dialysate introduction line and the dialysate discharge line, and the liquid pressure may not be accurately measured. Also, when the amount of introduced air is too large at the time of a liquid spill prevention operation, there is a problem in that a large amount of cleaning liquid or antiseptic liquid may be needed at the time of cleaning or disinfection of the dialysate introduction line and the dialysate discharge line.

It is to be noted that the problem as mentioned above may occurs not only in coupling tools that are respectively attached to the leading end of the dialysate introduction line and the leading end of the dialysate discharge line, but also in another coupling means (for instance, a cover member for opening and closing an extraction port formed in the dialysate introduction line) that allows free switching between a connected state which causes the dialysate introduction line and the dialysate discharge line to form a closed circuit, and an opened state which causes the closed circuit to be opened to form an opened portion.

The present teachings have been made in consideration of such a situation, and provides a blood purification apparatus capable of uniformizing the amount of air introduced through the opened portion at the time of a liquid spill prevention operation.

The teachings herein provide a blood purification apparatus comprising: a dialysate introduction line that is connectable to a blood purification means capable of purifying blood of a patient, circulated extracorporeally, and that allows dialysate to be introduced into the blood purification means; a dialysate discharge line that is connectable to the blood purification means, and that allows the dialysate introduced through the dialysate introduction line to be discharged from the blood purification means; a coupling means that allows free switching between a connected state which causes the dialysate introduction line and the dialysate discharge line to form a closed circuit, and an opened state which causes the closed circuit to be opened to form an opened portion; and a control means that, when the connected state is switched to the opened state by the coupling means, allows a liquid spill prevention operation to be performed, in which external air is introduced through the opened portion. An air detection means, by which air introduced through the opened portion is detectable, is provided in a vicinity of the coupling means, and the control means stops the liquid spill prevention operation when air is detected by the air detection means.

The teachings herein provide the blood purification apparatus according to the teachings herein, in which the air detection means has a pair of electrodes formed in a flow path of the dialysate introduction line or the dialysate discharge line, and is comprised of an electrical sensor that is electrically connectable via dialysate.

The teachings herein provide the blood purification apparatus according to the teachings herein, in which the pair of electrodes is attached to a valve means that allows the flow path of dialysate to be opened and closed, and the pair of electrodes is electrically connectable via dialysate when the valve means is in an opened state.

The teachings herein provide the blood purification apparatus according to the teachings herein, in which the air detection means is comprised of an optical sensor that includes a light emitting means that is capable of emitting light to a flow path of the dialysate introduction line or the dialysate discharge line, and a light receiving means that is capable of receiving the light emitted by the light emitting means.

The teachings herein provide the blood purification apparatus according to the teachings herein, in which the air detection means is comprised of an ultrasonic sensor that includes an oscillation means that is capable of oscillating ultrasonic waves to a flow path of the dialysate introduction line or the dialysate discharge line, and a reception means that is capable of receiving the ultrasonic waves oscillated by the oscillation means.

The teachings herein provide the blood purification apparatus according to the teachings herein, in which the liquid spill prevention operation includes an operation of opening a base end side of the dialysate introduction line or the dialysate discharge line, and when the closed circuit is switched to an opened state by the coupling means, a difference of height between the coupling tool and the dialysate introduction line or the dialysate discharge line causes dialysate to be discharged to an outside.

The teachings herein provide the blood purification apparatus according to the teachings herein, in which the coupling means is comprised of coupling tools that are respectively attached to a leading end of the dialysate introduction line and a leading end of the dialysate discharge line, connecting the coupling tools to each other causes the dialysate introduction line and the dialysate discharge line to form a closed circuit, and releasing connection between the coupling tools causes the closed circuit to be opened and the dialysate introduction line and the dialysate discharge line to be connectable to the blood purification means.

The teachings herein provide the blood purification apparatus according to the teachings herein, further comprising a retention means that is capable of retaining the coupling tools in a state in which the coupling tools are connected to each other, and a retention detection means that is capable of detecting retention or non-retention of the coupling tools by the retention means. The liquid spill prevention operation is triggered by detection of non-retention of the coupling tools by the retention means.

The teachings herein provide the blood purification apparatus according to the teachings herein, in which the dialysate introduction line includes an extraction port through which flowing dialysate is obtainable, and the coupling means is comprised of a cover member that when attached to the extraction port in a closed state of the extraction port, causes the dialysate introduction line and the dialysate discharge line to form a closed circuit, and when removed from the extraction port, opens the closed circuit.

According to the teachings herein, an air detection means, by which air introduced through the opened portion is detectable, is provided in a vicinity of the coupling means, and the control means stops the liquid spill prevention operation when air is detected by the air detection means. Thus, at the time of the liquid spill prevention operation, the amount of the air introduced through the opened portion can be uniformized.

According to the teachings herein, the air detection means has a pair of electrodes formed in a flow path of the dialysate introduction line or the dialysate discharge line, and is comprised of an electrical sensor that is electrically connectable via dialysate. Thus, the air introduced through the opened portion can be detected based on the conductive state of the pair of electrodes.

According to the teachings herein, the pair of electrodes is attached to a valve means that allows the flow path of dialysate to be opened and closed, and the pair of electrodes is electrically connectable via dialysate when the valve means is in an opened state. Thus, both the opened state of the valve means and the air introduced at the time of the liquid spill prevention operation can be detected based on the conductive state of the pair of electrodes.

According to the teachings herein, the air detection means is comprised of an optical sensor that includes a light emitting means that is capable of emitting light to a flow path of the dialysate introduction line or the dialysate discharge line, and a light receiving means that is capable of receiving the light emitted by the light emitting means. Thus, the air introduced through the opened portion can be detected based on the light receiving state assumed by the light receiving means. Therefore, in contrast to the case of the electrodes, the air detection means does not need to meet the flow path, and may be formed outside the flow path.

According to the teachings herein, the air detection means is comprised of an ultrasonic sensor that includes an oscillation means that is capable of oscillating ultrasonic waves to a flow path of the dialysate introduction line or the dialysate discharge line, and a reception means that is capable of receiving the ultrasonic waves oscillated by the oscillation means. Thus, the air introduced through the opened portion can be detected based on the receiving state assumed by the reception means. Therefore, the air detection means does not need to meet the flow path as in the case with the electrodes, and may be formed outside the flow path, and in contrast to the case of the optical sensor, the flow path does not need to be transparent or semi-transparent to allow light to transmit therethrough.

According to the teachings herein, the liquid spill prevention operation includes an operation of opening a base end side of the dialysate introduction line or the dialysate discharge line, and when the closed circuit is switched to an opened state by the coupling means, a difference of height between the coupling tool and the dialysate introduction line or the dialysate discharge line causes dialysate to be discharged to an outside. Thus, air can be introduced through the opened portion without driving an actuator or the like, and the liquid spill prevention operation can be easily performed.

According to the teachings herein, the coupling means is comprised of coupling tools that are respectively attached to a leading end of the dialysate introduction line and a leading end of the dialysate discharge line, connecting the coupling tools to each other causes the dialysate introduction line and the dialysate discharge line to form a closed circuit, and releasing connection between the coupling tools causes the closed circuit to be opened and the dialysate introduction line and the dialysate discharge line to be connectable to the blood purification means. Thus, liquid spill can be reliably prevented when connection between the coupling tools is released.

According to the teachings herein, the blood purification apparatus comprises a retention means that is capable of retaining the coupling tools in a state in which the coupling tools are connected to each other, and a retention detection means that is capable of detecting retention or non-retention of the coupling tools by the retention means. The liquid spill prevention operation is triggered by detection of non-retention of the coupling tools by the retention means. Thus, the liquid spill prevention operation can be performed at the timing of releasing connection between the coupling tools.

According to the teachings herein, the dialysate introduction line includes an extraction port through which flowing dialysate is obtainable, and the coupling means is comprised of a cover member that when attached to the extraction port in a closed state of the extraction port, causes the dialysate introduction line and the dialysate discharge line to form a closed circuit, and when removed from the extraction port, opens the closed circuit. Thus, liquid spill can be reliably prevented when the cover member is removed from the extraction port.

BRIEF DESCRIPTION OF THE DRAWINGS

FIG. 1 is a schematic diagram illustrating a blood purification apparatus according to an embodiment of the present invention.

FIG. 2 is a front view illustrating the external appearance of the blood purification apparatus.

FIG. 3 is a schematic view illustrating a retention means in the blood purification apparatus.

FIG. 4 is a schematic view illustrating a state in which coupling tools are connected in the blood purification apparatus.

FIG. 5 is a schematic view illustrating a state in which the coupling tools are held to the retention means in the blood purification apparatus.

FIG. 6 is a schematic view illustrating a state in which the coupling tools are connected to a dialyzer in the blood purification apparatus.

FIG. 7 is a schematic diagram including a blood circuit, illustrating a state in which the coupling tools are connected to the dialyzer in the blood purification apparatus.

FIG. 8 is a schematic diagram including a blood circuit, illustrating a state in which the coupling tools are connected to the dialyzer in the blood purification apparatus (liquid spill prevention operation).

FIG. 9 is a schematic diagram including a blood circuit, illustrating a state in which the coupling tools are connected to the dialyzer in the blood purification apparatus (liquid spill prevention operation).

FIG. 10 is a sectional view illustrating (front view) a state in which a cover member is attached to an extraction port to cover it in the blood purification apparatus.

FIG. 11 is a sectional view illustrating (side view) a state in which the cover member is attached to the extraction port to cover it in the blood purification apparatus.

FIG. 12 is a sectional view illustrating (front view) a state in which the cover member is removed from the extraction port in the blood purification apparatus.

FIG. 13 is a three view illustrating a valve means in the blood purification apparatus.

FIG. 14 is a sectional view taken along line XIV-XIV in FIG. 13.

FIG. 15 is a sectional view taken along line XV-XV in FIG. 13.

FIG. 16 is a sectional view taken along line XVI-XVI in FIG. 13.

FIG. 17 is a sectional view taken along line XVII-XVII in FIG. 13.

FIG. 18 is a flowchart illustrating the details of control performed by a control means of the blood purification apparatus.

FIG. 19 is a flowchart illustrating the details of control (dialysis preparation process) performed by the control means of the blood purification apparatus.

FIG. 20 is a schematic diagram illustrating another configuration (a type with one filter) in the blood purification apparatus.

FIG. 21 is a graph illustrating a voltage detected by an air detection means in the blood purification apparatus.

FIG. 22 is a schematic view illustrating another embodiment (an optical sensor is used as the air detection means) of the present invention.

FIG. 23 is a schematic view illustrating another embodiment (an ultrasonic sensor is used as the air detection means) of the present invention.

DETAILED DESCRIPTION

Hereinafter, an embodiment of the present invention will be specifically described with reference to the drawings.

A blood purification apparatus according to this embodiment is for extracorporeally circulating the blood of a patient to purify the blood, and is applied to a hemodialysis apparatus 1 (see FIG. 2) that is used in hemodialysis treatment. As illustrated in FIGS. 1 and 7, the hemodialysis apparatus 1 mainly includes a dialyzer 9 as a blood purification means; blood circuits (an arterial blood circuit 10 and a venous blood circuit 11) connected to the dialyzer 9; a dialysate introduction line L1 that is connectable to the dialyzer 9 and capable of introducing dialysate to the dialyzer 9; a dialysate discharge line L2 that is connectable to the dialyzer 9 and allows the dialysate introduced through the dialysate introduction line L1 to be discharged from the dialyzer; coupling tools C1, C2 (coupling tools referred to as so-called "coupling") as coupling means; a control means 30; and opening and closing valves such as electromagnetic valves V1 to V10. It is to be noted that instead of the electromagnetic valves V1 to V10 according to this embodiment, opening and closing valves in another configuration capable of opening and closing a flow path may be provided.

The blood circuits mainly includes an arterial blood circuit 10 and a venous blood circuit 11 comprised of a flexible tube, and the dialyzer 9 is connected to between the arterial blood circuit 10 and the venous blood circuit 11. The arterial blood circuit 10 has at its leading end connector (a) to which an arterial puncture needle is connectable, and a peristaltic blood pump 3 disposed at a midpoint. On the other hand, the venous blood circuit 11 has at its leading end connector b to which a venous puncture needle is connectable, and an air trap chamber 12 for bubble removal connected at a midpoint.

Then when the blood pump 3 is driven in a state in which the arterial puncture needle and the venous puncture needle are inserted in a patient, the blood of the patient reaches the dialyzer 9 through the arterial blood circuit 10, the blood is purified and water is removed by the dialyzer 9, then is returned to the body of the patient through the venous blood circuit 11 while bubbles are removed by the air trap chamber 12. Thus, the blood of the patient can be purified by the dialyzer 9 while being extracorporeally circulated through the blood circuits.

As illustrated in FIG. 6, in the case body of the dialyzer 9, a blood inlet port 9a, a blood outlet port 9b, a dialysate introduction port 9c, and a dialysate outlet port 9d are formed, and between these, the blood introduction port 9a is connected to the base end of the arterial blood circuit 10, and the blood outlet port 9b is connected to the base end of the venous blood circuit 11. Also, the dialysate introduction port 9c and the dialysate outlet port 9d are coupled to the dialysate introduction line L1 and the dialysate discharge line L2 via coupling tools C1, C2, respectively.

A plurality of hollow fibers are housed in the dialyzer 9, and the inside of each hollow fiber serves as a flow path of blood and a flow path of dialysate is provided between the outer circumferential surface of the hollow fiber and the inner circumferential surface of the case body. In the hollow fiber, there is formed a large number of fine holes (bores) through the outer circumferential surface and the inner circumferential surface, thus a hollow fiber membrane is formed, and the waste and excess water in the blood are designed to pass into dialysate through the membrane.

In addition, the dialysate introduction line L1 and the dialysate discharge line L2 are connected to a duplex pump 13 that delivers dialysate prepared to have a predetermined concentration to the dialyzer 9, and that discharges the waste along with dialysate from the dialyzer 9. Specifically, the duplex pump 13 is disposed to straddle the dialysate introduction line L1 and the dialysate discharge line L2, and a configuration is adopted in which driving the duplex pump 13 allows dialysate to be introduced via the dialysate introduction line L1 and dialysate to be discharged via the dialysate discharge line L2 into and from the dialyzer 9.

Also, the dialysate introduction line L1 is connected to electromagnetic valves V1, V4, V9, and filters 17, 18, and the dialysate introduced into the dialyzer 9 can be filtered by the filters 17, 18, and the flow path can be blocked or opened in any timing by the electromagnetic valves V1, V4, V9. On the upstream side (between the electromagnetic valve V9 and the filter 18) of the electromagnetic valve V9 in the dialysate introduction line L1, an extraction port 19, through which flowing dialysate is obtainable, is formed. It is to be noted that the dialysate introduction line L1 is connected to the dialysate discharge line L2 via bypass lines L3, L4, L5 to which the electromagnetic valves V3, V6, V10 are respectively connected.

As illustrated in FIGS. 10 to 12, the extraction port 19 is comprised of a port-shaped part that is connectable to a substitution line (not illustrated) or the like for coupling the dialysate introduction line L1 and the blood circuit. An inlet port T1 and an outlet port T2 are each formed in the extraction port 19, and the dialysate introduction line L1 is connected to each of the inlet port T1 and the outlet port T2. Thus, the dialysate introduced from the inlet port T1 is drawn from the outlet port T2 through the formed part in the extraction port 19.

Also, a cover member 20, which allows the extraction port 19 to be opened or closed, is attached to the extraction port 19. The cover member 20 includes a seal member 21 composed of a flexible member such as a resin material or a rubber material, and a cap member 22 that is composed of, for instance, a hard resin and that covers and retains the seal member 21. The seal member 21 and the cap member 22 are integrated. Thus, in a state in which the cover member 20 is attached to the extraction port 19, it is possible to prevent external leakage of the dialysate that flows through the dialysate introduction line L1.

Furthermore, as illustrated in FIGS. 10 to 12, the cover member 20 according to this embodiment is retained by a retention member 23 attached to a shaft member 24 which is movable up and down. As illustrated in FIG. 12, raising the retention member 23 causes the cover member 20 to be removed from the extraction port 19, and as illustrated in FIGS. 10 and 11, lowering the retention member 23 causes the cover member 20 to be attached to the extraction port 19. It is to be noted that symbol R in FIGS. 10 to 12 indicates a lock means that locks the retention member 23 in a state in which the cover member 20 is attached to the extraction port 19.

Also, the dialysate discharge line L2 is connected to detour lines L6, L7 to make a detour around the duplex pump 13, and an ultrafiltration pump 14 is connected to the detour line L6. Thus, it is designed that driving the ultrafiltration pump 14 in a process of extracorporeally circulating the blood of a patient in the blood circuit allows water in the blood flowing through the dialyzer 9 to be removed from the blood. Furthermore, on the upstream side (the right side in FIGS. 1, 7) of the duplex pump 13 in the dialysate discharge line L2, a pressurizing pump 15 is connected, that makes liquid pressure adjustment of the dialysate discharge line L2 in the duplex pump 13 (the liquid delivery pump), and a detour line L8 is extended via a chamber 16 from between the pressurizing pump 15 and the duplex pumps 13.

Furthermore, on the downstream side (between a connection portion of the bypass line L4 and a connection portion of the bypass line L5) of the electromagnetic valve V5 in the dialysate discharge line L2, a pressure detection means T is connected, comprised of a sensor that can detect a pressure (liquid pressure in a flow path) in a flow path. In addition, the dialysate discharge line L2 and the detour lines L7, L8 branched therefrom are connected to electromagnetic valves V2, V5, V7, V8, and a flow path of dialysate can be blocked or opened in any timing.

The electromagnetic valves (V1 to V10) allow flow paths of dialysate to be opened or closed in any manner by energization, and as illustrated in FIGS. 13 to 17, the electromagnetic valves (V4 to V10) between these are configured to include an inlet port Pa and an outlet port Pb, a moving core 25 formed in a solenoid 29, a diaphragm 26 attached to the tip of the moving core 25, a body 27 attached to the solenoid 29, and an inlet port-side electrode (Da) and an outlet port-side electrode Db attached to the body 27.

In the body 27, there are formed an inlet-side flow path W1 which communicates with the inlet port Pa, and outlet-side flow paths W2, W3 which communicate with the outlet port (Pb), and the inlet-side flow path W1 and the outlet-side flow path W2 can communicate with each other via an opening 27a. It is to be noted that as illustrated in FIG. 16, the outlet-side flow path W2 is formed of window parts 27b, which communicates with the opening 27a, in the body 27, and the outlet-side flow path W2 communicates with the outlet-side flow path W3 which communicates with the outlet port (Pb). The opening 27a can be opened or closed by the diaphragm 26, and a flow path is closed in a closed state, and a flow path is opened in an opened state to allow flow of liquid.

When the solenoid 29 is in a non-energized state, the moving core 25 is urged by the urging force of a spring 28 in a direction in which the opening 27a is closed by the diaphragm 26. When the solenoid 29 is energized, the moving core 25 moves against the urging force of the spring 28 to open the opening 27a, and thus the dialysate introduced from the inlet port (Pa) reaches the outlet-side flow path W3 via the inlet-side flow path W1 and the outlet-side flow path W2, and is drawn from the outlet port Pb.

The inlet port-side electrode Da and the outlet port-side electrode Db are comprised of a pair of electrodes that are mounted to meet the inlet-side flow path W1 and the outlet-side flow path W3, and when an electromagnetic valve (V4 to V10) is set to an opened state, the electrodes are electrically connectable via dialysate flowing through the inlet-side flow path W1 and the outlet-side flow path W3. Thus, in a state in which conduction between the inlet port-side electrode (Da) and the outlet port-side electrode Db is detected, it is determined that the electromagnetic valve is in an opened state (the opening 27a is set to an opened state by the diaphragm 26), and in a state in which the conduction is not detected, it is determined that the electromagnetic valve is in a closed state (the opening 27a is set to a closed state).

On the other hand, as illustrated in FIGS. 4 to 6, the coupling tools C1, C2 are attached to the leading end of the dialysate introduction line L1 and the leading end of the dialysate discharge line L2 according to this embodiment. Connection (see FIG. 5) between the coupling tools C1, C2 causes the dialysate introduction line L1 and the dialysate discharge line L2 to form a closed circuit, and releasing the connection between the coupling tools C1, C2 causes the closed circuit to be opened and the coupling tools C1, C2 can be coupled (see FIG. 6) to the dialyzer 9. That is, the coupling tools C1, C2 (coupling means of the present invention) according to this embodiment allow free switching between a connected state which causes the dialysate introduction line L1 and the dialysate discharge line L2 to form a closed circuit, and an opened state which causes the closed circuit to be opened to form an opened portion (in this embodiment, openings of the coupling tools C1, C2, which communicate with the outside when the connection is released).

Furthermore, as illustrated in FIG. 2, in the hemodialysis apparatus 1 according to this embodiment, there are disposed a display means 2 for displaying the settings for treatment and the conditions of a patient in a treatment process, a substitution pump 4 for substitution, an air bubble detection sensor 5 that can detect an air bubble in the blood circuit, a warning light 6, a coupling tool receiver 7 (retention means), a bypass switch 8 (retention detection means). The coupling tool receiver 7 is comprised of a hook-shaped part attached to the hemodialysis apparatus 1, and as illustrated in FIG. 5, is configured to retain the coupling tools C1, C2 in a state in which the coupling tools C1, C2 are connected to each other. As illustrated in FIG. 3, the bypass switch 8 is comprised of a switch attached to the coupling tool receiver 7, and is configured to be able to detect retention and non-retention of the coupling tools C1, C2 by electrically switching when the coupling tools C1, C2 in a mutually connected state are retained by the coupling tool receiver 7.

The control means 30 is comprised of a microcomputer and the like disposed in a dialysis device 1, and is configured to be able to perform opening and closing control of the electromagnetic valves (V1 to V10) before or after a treatment or during a treatment, control of an actuator such as the duplex pump 13 and the ultrafiltration pump 14, and others. In particular, when the connected state is switched to the opened state by releasing connection between the coupling tools C1, C2, the control means 30 according to this embodiment allows a liquid spill prevention operation to be performed, in which external air is introduced through the opened portion (the openings of the coupling tools C1, C2). That is to say, when connection between the coupling tools C1, C2 is released, leakage of dialysate to the outside can be avoided by introducing external air through the openings of the coupling tools C1, C2.

Here, in this embodiment, a configuration is adopted in which an air detection means, by which air introduced through the opened portion (the openings of the coupling tools C1, C2) is detectable, is provided in the vicinity of the coupling tool C1 or the coupling tool C2, and the control means 30 stops the liquid spill prevention operation under the condition that air is detected by the air detection means. The air detection means according to this embodiment includes a pair of electrodes (the inlet port-side electrode Da and the outlet port-side electrode Db) disposed at the electromagnetic valve V9 (the vicinity of the coupling tool C1 at the leading end of the dialysate introduction line L1) and the electromagnetic valve V5 (the vicinity of the coupling tool C2 at the leading end of the dialysate discharge line L2).

That is, the air detection means according to this embodiment is configured to include a pair of electrodes (the inlet port-side electrode Da and the outlet port-side electrode Db) attached to valve means (the electromagnetic valves V5, V9) that allows the flow path of dialysate to be opened and closed. When the valve means is in an opened state, the pair of electrodes is electrically connectable via dialysate, and when the valve means (the electromagnetic valves V5, V9) is in a closed state or when air is present between the pair of electrodes even in an opened state, the pair of electrodes is not electrically connectable. Thus, the liquid spill prevention operation is performed, and the valve means (V5, V9) are set to an opened state, and when air is introduced through the opened portion of the coupling tools C1, C2, arrival of the air at the valve means blocks electrical connection between the pair of electrodes, and thus the air can be detected.

Also, the liquid spill prevention operation performed by the control of the control means 30 has an operation of opening the base end side of the dialysate introduction line L1 or the dialysate discharge line L2, and when the closed circuit is switched to an opened state by the coupling tools C1, C2, a difference of height between the coupling tools C1, C2 and the dialysate introduction line L1 or the dialysate discharge line L2 causes dialysate to be discharged to the outside. Thus, air can be introduced through the opened portion without driving an actuator or the like, and the liquid spill prevention operation can be easily performed.

Furthermore, the liquid spill prevention operation performed by the control of the control means 30 is triggered by detection of non-retention (a state in which the coupling tools C1, C2 are not retained by the coupling tool receiver 7) of the coupling tools C1, C2 by the coupling tool receiver 7 using the bypass switch 8 (retention detection means). That is, when connection between the coupling tools C1, C2 is released and the coupling tools C1, C2 are coupled to the dialyzer 9, the coupling tools C1, C2 need to be raised from the coupling tool receiver 7, and thus when non-retention of the coupling tools C1, C2 by the coupling tool receiver 7 is detected, it is presumed that subsequently, the connection between the coupling tools C1, C2 is released and the closed circuit assumes an opened state. Consequently, with the liquid spill prevention operation triggered by the non-retention, liquid spill can be reliably prevented when the state is changed to an opened state.

Thus, by performing the liquid spill prevention operation as described above, when the connection between the coupling tools C1, C2 is released, air is introduced through the openings (the openings of the coupling tools C1, C2, which communicate with the outside when the connection is released) of the coupling tools C1, C2, and thus spilling of dialysate through the openings can be prevented. Furthermore, when air enters between a pair of electrodes (the inlet port-side electrode Da and the outlet port-side electrode Db) formed at the electromagnetic valves V5, V9 in a state in which the electromagnetic valves V5, V9 are set to an opened state, as illustrated by graph (α) of FIG. 21, the voltage across the pair of electrodes is decreased from a predetermined value to 0 value (or near 0 value). Therefore, when the liquid spill prevention operation is stopped at time t at which the voltage across the pair of electrodes is decreased to near 0, subsequent introduction of air can be blocked, and the amount of introduced air can be uniformizd. It is to be noted that symbol (β) in FIG. 21 indicates the timing at which the liquid spill prevention operation is performed, and the liquid spill prevention operation is started at a time at which a lower value changes to a higher value.

Next, the control performed by the control means 30 according to this embodiment will be described based on the flowcharts of FIGS. 18 and 19.

First, in cleaning process S1, water cleaning is performed in which RO water is passed through the pipes (such as the dialysate introduction line L1 and the dialysate discharge line L2) in the hemodialysis apparatus 1, and medicinal solution disinfection is performed in which a solution obtained by mixing pharmacological agent such as medicinal solution for disinfection with clean water is passed through the pipes. Then, the flow proceeds to preset process S2, and a standby state is maintained until the next liquid substitution process S3 is started. In the liquid substitution process S3, the dialysate is substituted for the liquid in the pipes of the hemodialysis apparatus 1, and in dialysis preparation process S4 described in detail later, a preparation step for making dialysis treatment is performed. It is to be noted that the coupling tools C1, C2 are connected in the cleaning process S1 until an opened state is assumed in the dialysis preparation process S4, and the pipe including the dialysate introduction line L1 and the dialysate discharge line L2 forms a closed circuit.

When the dialysis preparation process S4 is completed, an arterial puncture needle coupled to the leading end of the arterial blood circuit 10 and a venous puncture needle coupled to the leading end of the venous blood circuit 11 are inserted into a patient, and the blood pump 3 is driven, thereby performing blood removal process S5. Subsequently, the duplex pump 13, the ultrafiltration pump 14 and the like are driven, thereby performing treatment process S6 is performed, in which the blood of the patient is extracorporeally circulated in the blood circuit to purify the blood. After the hemodialysis treatment by the treatment process S6 is completed, blood return process S7 is performed in which the blood in the blood circuit is returned to the patient, the puncture needles are pulled out from the patient, then in drain liquid process S8, the dialysate in the pipes of the hemodialysis apparatus 1 is discharged to the outside. So far, a series of processes related to treatment and its preparation is completed.

Next, the specific process of the dialysis preparation process S4 will be described.

First, as indicated in FIG. 19, it is determined whether or not a liquid spill prevention operation has been performed (S4a). When it is determined that a liquid spill prevention operation has not been performed, it is determined whether or not the bypass switch 8 has been set to OFF (in other words, a state in which the coupling tools C1, C2 are not retained by the coupling tool receiver 7 is detected) from ON (S4b). When it is determined at S4b that the bypass switch 8 has been set to OFF, the flow proceeds to S4c, and as indicated in FIG. 8, the electromagnetic valves V2, V4, V5, V7 are set to an opened state and the base end side of the dialysate discharge line L2 is opened. It is to be noted that at this point, the duplex pump 13 is stopped.

Subsequently, the flow proceeds to S4d, and it is determined whether or not two filters (the filters 17, 18) are attached to the dialysate introduction line L1 as in the hemodialysis apparatus 1 according to this embodiment. When it is determined that two filters are attached, the flow proceeds to S4e, and as illustrated in FIG. 9, the electromagnetic valve V10 is set to a closed state, and the electromagnetic valves V6, V9 are set to an opened state. It is to be noted that as a hemodialysis apparatus in which one filter is attached to the dialysate introduction line L1, the counterpart (only the filter 17 is connected) illustrated in FIG. 20 may be presented. When treatment is made by such a hemodialysis apparatus, after the determination of S4d, the flow proceeds to S4f, and V6 is set to an opened state. Thus, the liquid spill prevention operation is performed by proceeding from S4c to S4e or from S4c to S4f.

After the liquid spill prevention operation is started as described above, it is determined whether or not air is detected by the air detection means (the inlet port-side electrode Da and the outlet port-side electrode Db) (S4g). Specifically, since the base end side of the dialysate discharge line L2 is opened, when connection between the coupling tools C1, C2 is released, air is introduced through the openings of the coupling tools C1, C2, and if the introduced air arrives at the electromagnetic valves V5, V9, the voltage across the pair of electrodes (the inlet port-side electrode Da and the outlet port-side electrode Db) is decreased to near 0 value as the time t indicated by graph (α) of FIG. 21. Thus, air is detected by detecting the voltage.

When it is determined in S4g that air is detected by the air detection means, the flow proceeds to S4j, and the electromagnetic valves V5, V9 are set to a closed state, thereby stopping the liquid spill prevention operation. On the other hand, when air is not detected in S4g, the flow proceeds to S4h, and it is determined whether or not a predetermined time has elapsed since the liquid spill prevention operation is started. When a predetermined time has elapsed, the flow proceeds to S4i, and one of unreleased connection between the coupling tools C1, C2, a failure of the electromagnetic valves V5 or V9, and a failure of the inlet port-side electrode (Da) and the outlet port-side electrode (Db) is notified. So far, the dialysis preparation process S4 is completed.

According to the embodiment described above, the air detection means (the inlet port-side electrode (Da) and the outlet port-side electrode (Db)), by which air introduced through the opened portion is detectable, is provided in the vicinity of the coupling tools C1, C2, and the control means 30 stops the liquid spill prevention operation under the condition that air is detected by the air detection means. Thus, the amount of air introduced through the opened portion can be uniformizd at the time of the liquid spill prevention operation.

Also, the air detection means according to this embodiment has a pair of electrodes (the inlet port-side electrode (Da) and the outlet port-side electrode (Db)) formed in a flow path of the dialysate introduction line or the dialysate discharge line, and is comprised of an electrical sensor that is electrically connectable via dialysate. Thus, air introduced through the opened portion can be detected based on the conductive state of the pair of electrodes. Furthermore, the pair of electrodes included in the air detection means is attached to the valve means (the electromagnetic valves V5, V9) that allows the flow path of dialysate to be opened and closed, and the pair of electrodes is electrically connectable via dialysate when the valve means is in an opened state. Thus, both the opened state of the valve means and the air introduced at the time of the liquid spill prevention operation can be detected based on the conductive state of the pair of electrodes.

The coupling means is comprised of the coupling tools C11, C2 that are respectively attached to the leading end of the dialysate introduction line L1 and the leading end of the dialysate discharge line L2, connecting the coupling tools C1, C2 to each other causes the dialysate introduction line L1 and the dialysate discharge line L2 to form a closed circuit, and releasing the connection between the coupling tools C1, C2 causes the closed circuit to be opened and the coupling tools C1, C2 can be coupled to the dialyzer 9. Thus, liquid spill can be reliably prevented when the connection between the coupling tools C1, C2 is released.

Although the embodiment has been described so far, the present invention is not limited to this, and for instance, the air detection means may have another configuration. Specifically, although the air introduced by a liquid spill prevention operation is detected by a pair of electrodes attached to the valve means (the electromagnetic valves V5, V9) in this embodiment, the pair of electrodes may not be attached to a valve means such as an electromagnetic valve as long as the electrodes are mounted to meet the flow path of dialysate and are electrically connectable via dialysate.

Also, instead of the electrical sensor having a pair of electrodes as described above, as illustrated in FIG. 22, an air detection means may be used that is comprised of an optical sensor including a light emitting means E1 that is capable of emitting light to the flow path of the dialysate introduction line L1 or the dialysate discharge line L2, and a light receiving means E2 that is capable of receiving light emitted by the light emitting means. In this case, the air introduced through the opened portion can be detected based on the light receiving state assumed by the light receiving means E2. Thus, the air detection means does not need to meet the flow path as in the case with the electrodes, and may be formed outside the flow path.

In addition, instead of the electrical sensor or optical sensor as described above, as illustrated in FIG. 23, an air detection means may be used that is comprised of an ultrasonic sensor including an oscillation means F1 that is capable of oscillating ultrasonic waves to the flow path of the dialysate introduction line L1 or the dialysate discharge line L2, and a reception means F2 that is capable of receiving ultrasonic waves oscillated by the oscillation means. In this case, the air introduced through the opened portion can be detected based on the receiving state assumed by the receiving means F2. Thus, the air detection means does not need to meet the flow path as in the case with the electrodes, and may be formed outside the flow path, and in contrast to the case of the optical sensor, the flow path does not need to be transparent or semi-transparent to allow light to transmit therethrough.

It is to be noted that the liquid spill prevention operation according to this embodiment has an operation of opening the base end side of the dialysate introduction line L1 or the dialysate discharge line L2, and when the closed circuit is switched to an opened state by releasing connection between the coupling tools C1, C2, a difference of height between the coupling tools C1, C2 and the dialysate introduction line L1 or the dialysate discharge line L2 causes dialysate to be discharged to the outside. However, an actuator such as the duplex pump 13, the ultrafiltration pump 14 or the pressurizing pump 15 may be driven, and when the closed circuit is switched to an opened state by releasing connection between the coupling tools C1, C2, the dialysate in the closed circuit may be discharged to the outside.

Furthermore, although the coupling means according to this embodiment is comprised of the coupling tools C1, C2, the coupling means may be comprised of, for instance, a cover member 20 that, when mounted in a closed state of the extraction port 19, the dialysate introduction line L1 and the dialysate discharge line L2 form a closed circuit, and when removed from the extraction port 19, the closed circuit is opened. In this case, liquid spill can be reliably prevented when the cover member 20 is removed from the extraction port 19. That is, the cover member 20 allows free switching between a connected state which causes the dialysate introduction line L1 and the dialysate discharge line L2 to form a closed circuit in a connected state of the coupling tools C1, C2, and an opened state which causes the closed circuit to be opened to form an opened portion (the extraction port 19 is set to an opened state). At the time of the liquid spill prevention operation, air is introduced through the extraction port 19 and liquid spill can be prevented. It is to be noted that when the cover member 20 is used as the coupling means, the air detection means is disposed in the vicinity (for instance, a pair of electrodes of the electromagnetic valves V4, V10) of the cover member 20.

It is to be noted that the blood purification apparatus to which this embodiment is applicable may have any configuration, and for instance, dialysate is introduced or discharged by a chamber instead of the duplex pump 13, or a blood purification means in another configuration is provided instead of the dialyzer 9. Furthermore, in this embodiment, the invention is applied to the hemodialysis apparatus 1. However, the invention may be applied to a blood purification apparatus that performs another blood purification treatment.

As long as a blood purification apparatus includes an air detection means, by which air introduced through the opened portion is detectable, is provided in the vicinity of the coupling means, and a control means stops the liquid spill prevention operation when air is detected by the air detection means, the invention is applicable to the blood purification apparatus with a different external appearance form or having another function added.

REFERENCE SIGN LIST 1 hemodialysis apparatus (blood purification apparatus)
2 display means
3 blood pump
4 substitution pump
5 air bubble detection sensor
6 warning light
7 coupling tool receiver (retention means)
8 bypass switch (retention detection means)
9 dialyzer (blood purification means)
10 arterial blood circuit
11 venous blood circuit
12 air trap chamber
13 duplex pump
14 ultrafiltration pump
15 pressurizing pump
16 chamber
17, 18 filter
19 extraction port 20 cover member
21 seal member
22 cap member
23 retention member
24 shaft member
25 moving core
26 diaphragm
27 body
28 spring
29 solenoid
30 control means
L1 dialysate introduction line
L2 dialysate discharge line
C1, C2 coupling tool (coupling means)

The invention claimed is:

1. A blood purification apparatus comprising:
a blood purification device that is capable of purifying blood of a patient, circulated extracorporeally;
a dialysate introduction line that is connectable to the blood purification device, and that allows dialysate to be introduced into the blood purification device;
a dialysate discharge line that is connectable to the blood purification device, and that allows the dialysate introduced through the dialysate introduction line to be discharged from the blood purification device;
a coupling means that allows free switching between a connected state which causes the dialysate introduction line and the dialysate discharge line to form a closed circuit, and an opened state which causes the closed circuit to be opened to form an opened portion; and
a control means that, when the connected state is switched to the opened state by the coupling means, allows a liquid spill prevention operation to be performed, in which external air is introduced through the opened portion,
wherein an air detection means, by which air introduced through the opened portion is detectable, is provided in a vicinity of the coupling means, and the control means stops the liquid spill prevention operation when air is detected by the air detection means.

2. The blood purification apparatus according to claim 1, wherein the air detection means has a pair of electrodes formed in a flow path of the dialysate introduction line or the dialysate discharge line, and is comprised of an electrical sensor that is electrically connectable via dialysate.

3. The blood purification apparatus according to claim 2, wherein the pair of electrodes is attached to a valve means that allows the flow path of dialysate to be opened and closed, and the pair of electrodes is electrically connectable via dialysate when the valve means is in an opened state.

4. The blood purification apparatus according to claim 1, wherein the air detection means is comprised of an optical sensor that includes a light emitting means that is capable of emitting light to a flow path of the dialysate introduction line or the dialysate discharge line, and a light receiving means that is capable of receiving the light emitted by the light emitting means.

5. The blood purification apparatus according to claim 1, wherein the air detection means is comprised of an ultrasonic sensor that includes an oscillator that is capable of oscillating ultrasonic waves to a flow path of the dialysate introduction line or the dialysate discharge line, and a receiver that is capable of receiving the ultrasonic waves oscillated by the oscillator.

6. The blood purification apparatus according to claim 1, wherein the liquid spill prevention operation includes an operation of opening a base end side of the dialysate introduction line or the dialysate discharge line, and when the closed circuit is switched to an opened state by the coupling means, a difference of height between a coupling tool and the dialysate introduction line or the dialysate discharge line causes dialysate to be discharged to an outside.

7. The blood purification apparatus according to claim 1, wherein the coupling means is comprised of coupling tools that are respectively attached to a leading end of the dialysate introduction line and a leading end of the dialysate discharge line, connecting the coupling tools to each other causes the dialysate introduction line and the dialysate discharge line to form a closed circuit, and releasing connection between the coupling tools causes the closed circuit to be opened and the dialysate introduction line and the dialysate discharge line to be connectable to the blood purification device.

8. The blood purification apparatus according to claim 7, further comprising a retention means that is capable of retaining the coupling tools in a state in which the coupling tools are connected to each other, and a retention detection means that is capable of detecting retention or non-retention of the coupling tools by the retention means,
wherein the liquid spill prevention operation is triggered by detection of non-retention of the coupling tools by the retention means.

9. The blood purification apparatus according to claim 1, wherein the dialysate introduction line includes an extraction port through which flowing dialysate is obtainable, and the coupling means is comprised of a cover member that when attached to the extraction port in a closed state of the extraction port, causes the dialysate introduction line and the dialysate discharge line to form a closed circuit, and when removed from the extraction port, opens the closed circuit.

10. The blood purification apparatus according to claim 2, wherein the liquid spill prevention operation includes an operation of opening a base end side of the dialysate introduction line or the dialysate discharge line, and when the closed circuit is switched to an opened state by the coupling means, a difference of height between a coupling tool and the dialysate introduction line or the dialysate discharge line causes dialysate to be discharged to an outside.

11. The blood purification apparatus according to claim 3, wherein the liquid spill prevention operation includes an operation of opening a base end side of the dialysate introduction line or the dialysate discharge line, and when the closed circuit is switched to an opened state by the coupling means, a difference of height between a coupling tool and the dialysate introduction line or the dialysate discharge line causes dialysate to be discharged to an outside.

12. The blood purification apparatus according to claim 2, wherein the coupling means is comprised of coupling tools that are respectively attached to a leading end of the dialysate introduction line and a leading end of the dialysate discharge line, connecting the coupling tools to each other causes the dialysate introduction line and the dialysate discharge line to form a closed circuit, and releasing connection between the coupling tools causes the closed circuit to be opened and the dialysate introduction line and the dialysate discharge line to be connectable to the blood purification device.

13. The blood purification apparatus according to claim 3, wherein the coupling means is comprised of coupling tools that are respectively attached to a leading end of the dialysate introduction line and a leading end of the dialysate discharge line, connecting the coupling tools to each other causes the dialysate introduction line and the dialysate discharge line to form a closed circuit, and releasing connection between the coupling tools causes the closed circuit to be opened and the dialysate introduction line and the dialysate discharge line to be connectable to the blood purification device.

14. The blood purification apparatus according to claim 11, wherein the coupling means is comprised of coupling tools that are respectively attached to a leading end of the dialysate introduction line and a leading end of the dialysate discharge line, connecting the coupling tools to each other causes the dialysate introduction line and the dialysate discharge line to form a closed circuit, and releasing connection between the coupling tools causes the closed circuit to be opened and the dialysate introduction line and the dialysate discharge line to be connectable to the blood purification device.

15. The blood purification apparatus according to claim 2, wherein the dialysate introduction line includes an extraction port through which flowing dialysate is obtainable, and the coupling means is comprised of a cover member that when attached to the extraction port in a closed state of the extraction port, causes the dialysate introduction line and the dialysate discharge line to form a closed circuit, and when removed from the extraction port, opens the closed circuit.

16. The blood purification apparatus according to claim 3, wherein the dialysate introduction line includes an extraction port through which flowing dialysate is obtainable, and the coupling means is comprised of a cover member that when attached to the extraction port in a closed state of the extraction port, causes the dialysate introduction line and the dialysate discharge line to form a closed circuit, and when removed from the extraction port, opens the closed circuit.

17. The blood purification apparatus according to claim 14, wherein the dialysate introduction line includes an extraction port through which flowing dialysate is obtainable, and the coupling means is comprised of a cover member that when attached to the extraction port in a closed state of the extraction port, causes the dialysate introduction line and the dialysate discharge line to form a closed circuit, and when removed from the extraction port, opens the closed circuit.

* * * * *